United States Patent
Balaji et al.

(10) Patent No.: US 12,257,368 B2
(45) Date of Patent: Mar. 25, 2025

(54) EPITHELIALIZING MICROPOROUS BIOMATERIAL FOR USE IN AVASCULAR ENVIRONMENTS AND IN CORNEAL IMPLANTS

(71) Applicant: W. L. Gore & Associates, Inc., Newark, DE (US)

(72) Inventors: Gopalan V. Balaji, Kennett Square, PA (US); Paul J. Fischer, Wilmington, DE (US); Thomas B. Schmiedel, Middletown, DE (US); Anuraag Singh, Hockessin, DE (US)

(73) Assignee: W. L. Gore & Associates, Inc., Newark, DE (US)

( * ) Notice: Subject to any disclaimer, the term of this patent is extended or adjusted under 35 U.S.C. 154(b) by 988 days.

(21) Appl. No.: 17/252,036

(22) PCT Filed: Jun. 14, 2019

(86) PCT No.: PCT/US2019/037301
§ 371 (c)(1),
(2) Date: Dec. 14, 2020

(87) PCT Pub. No.: WO2019/241700
PCT Pub. Date: Dec. 19, 2019

(65) Prior Publication Data
US 2021/0252194 A1    Aug. 19, 2021

Related U.S. Application Data

(60) Provisional application No. 62/684,843, filed on Jun. 14, 2018.

(51) Int. Cl.
A61L 27/56 (2006.01)
A61L 27/16 (2006.01)
A61L 27/34 (2006.01)
A61L 27/44 (2006.01)

(52) U.S. Cl.
CPC ............... *A61L 27/56* (2013.01); *A61L 27/16* (2013.01); *A61L 27/34* (2013.01); *A61L 27/44* (2013.01); *A61L 2400/18* (2013.01); *A61L 2430/16* (2013.01)

(58) Field of Classification Search
None
See application file for complete search history.

(56) References Cited

U.S. PATENT DOCUMENTS

| | | |
|---|---|---|
| 3,953,566 A | 4/1976 | Gore |
| 4,693,715 A | 9/1987 | Robert |
| 4,865,601 A | 9/1989 | Caldwell et al. |
| 5,041,225 A | 8/1991 | Norman |
| 5,100,689 A | 3/1992 | Goldberg et al. |
| 5,108,428 A | 4/1992 | Capecchi et al. |
| 5,183,545 A | 2/1993 | Branca et al. |
| 5,282,851 A | 2/1994 | Jacob-LaBarre |
| 5,300,115 A | 4/1994 | Py |
| 5,300,116 A | 4/1994 | Chirila et al. |
| 5,321,109 A | 6/1994 | Bosse et al. |
| 5,462,781 A | 10/1995 | Zukowski |
| 5,476,589 A | 12/1995 | Bacino |
| 5,708,044 A | 1/1998 | Branca |
| 5,902,745 A | 5/1999 | Butler et al. |
| 6,102,946 A | 8/2000 | Nigam |
| 6,106,552 A | 8/2000 | Lacombe et al. |
| 6,391,055 B1 | 5/2002 | Ikada et al. |
| 6,541,589 B1 | 4/2003 | Baillie |
| 6,818,018 B1 | 11/2004 | Sawhney |
| 6,976,997 B2 | 12/2005 | Noolandi et al. |
| 7,049,380 B1 | 5/2006 | Chang et al. |
| 7,306,729 B2 | 12/2007 | Strid et al. |
| 7,531,611 B2 | 5/2009 | Sabol et al. |

(Continued)

FOREIGN PATENT DOCUMENTS

| | | |
|---|---|---|
| CN | 1939957 A | 4/2007 |
| CN | 102283720 A | 12/2011 |

(Continued)

OTHER PUBLICATIONS

Barber et al., "The acceptance of a vitreous carbon alloplastic material, Proplast, in the rabbit eye," Invest. Ophthalmol. Vis. Sci., 19:182-191, (1980).
Barber, "Keratoprosthesis: past and present," Int. Ophthalmol. Clin., 28:103-109, (1988).
Bhasin et al., "Integrating Keratoprosthesis, Chapter 26 in Keratoprostheses and Artificial Corneas: Fundamentals and Surgical Applications," Cortina MS and de la Cruz J. (Eds.) Springer Verlag, New York, 2015.
Essen et al., "Biocompatibility of a fish scale-derived artificial cornea: Cytotoxicity cellular adhesion and phenotype, and in vivo immunogenicity", Biomaterials, vol. 81, (2016), pp. 36-45.

(Continued)

*Primary Examiner* — Jennifer Chin
(74) *Attorney, Agent, or Firm* — Nelson Mullins Riley & Scarborough LLP

(57) ABSTRACT

A microporous biocomposite that is suitable for surgical implantation in an avascular environment is provided. The microporous biocomposite includes (1) a polymer scaffold having a thickness less than about 100 μm and nodal structures that extend to at least one surface of the polymer scaffold and (2) a hydrophilic coating on the polymer scaffold. In some embodiments, the porous scaffold is a microporous biomaterial with nodal structures that extend from a first surface to a second surface of the microporous biomaterial. The hydrophilic coating may be a node and fibril coating. The microporous biocomposite allows for the integration and sustained viability of epithelial cells on the surface thereof as well as tissue integration and the internal colonization of the biomaterial with other cell types, such as keratocytes and fibroblasts. In at least one embodiment, the microporous biocomposite may be incorporated into an artificial corneal implant or in other avascular mesoplants.

20 Claims, 11 Drawing Sheets

(56) References Cited

U.S. PATENT DOCUMENTS

| | | | |
|---|---|---|---|
| 7,615,282 | B2 | 11/2009 | Lutz et al. |
| 7,740,020 | B2 | 6/2010 | Lutz et al. |
| 7,932,184 | B2 | 4/2011 | Ishii |
| 8,048,440 | B2 | 11/2011 | Chang et al. |
| 8,637,144 | B2 | 1/2014 | Ford |
| 9,139,669 | B2 | 9/2015 | Xu et al. |
| 9,441,088 | B2 | 9/2016 | Sbriglia et al. |
| 9,849,629 | B2 | 12/2017 | Zagl et al. |
| 9,926,416 | B2 | 3/2018 | Sbriglia |
| 9,932,429 | B2 | 4/2018 | Sbriglia |
| 2002/0007217 | A1 | 1/2002 | Jacob et al. |
| 2003/0225439 | A1 | 12/2003 | Cook et al. |
| 2003/0232198 | A1 | 12/2003 | Lamberti et al. |
| 2004/0049268 | A1 | 3/2004 | Noolandi et al. |
| 2004/0173978 | A1 | 9/2004 | Bowen et al. |
| 2006/0025852 | A1 | 2/2006 | Armstrong et al. |
| 2006/0047311 | A1 | 3/2006 | Lutz et al. |
| 2007/0075013 | A1 | 4/2007 | Duong et al. |
| 2007/0168025 | A1 | 7/2007 | Darougar et al. |
| 2008/0150177 | A1 | 6/2008 | Hook et al. |
| 2008/0255663 | A1 | 10/2008 | Akpek et al. |
| 2009/0182421 | A1 | 7/2009 | Silvestrini et al. |
| 2011/0125260 | A1 | 5/2011 | Shen |
| 2011/0280952 | A1 | 11/2011 | Caramella et al. |
| 2013/0090612 | A1 | 4/2013 | De Juan et al. |
| 2013/0184554 | A1 | 7/2013 | Elsheikh et al. |
| 2014/0121612 | A1 | 5/2014 | Alster et al. |
| 2015/0216651 | A1 | 8/2015 | Parel et al. |
| 2015/0223930 | A1 | 8/2015 | Shiuey |
| 2016/0167291 | A1 | 6/2016 | Zagl et al. |
| 2016/0367947 | A1 | 12/2016 | Hollenbaugh et al. |
| 2021/0244528 | A1 | 8/2021 | Balaji et al. |

FOREIGN PATENT DOCUMENTS

| | | |
|---|---|---|
| EP | 2136737 A2 | 12/2009 |
| FR | 2649605 A1 | 1/1991 |
| JP | 46-003112 B | 1/1971 |
| JP | 2000-503870 A | 4/2000 |
| JP | 2000-325369 A | 11/2000 |
| JP | 2002-533159 A | 10/2002 |
| JP | 2005-527330 A | 9/2005 |
| JP | 2010-523266 A | 7/2010 |
| JP | 2013-540521 A | 11/2013 |
| JP | 2013-544558 A | 12/2013 |
| JP | 2014-050755 A | 3/2014 |
| MX | 2013011483 A | 4/2015 |
| SG | 188155 A1 | 3/2013 |
| WO | 2004/028410 A1 | 4/2004 |
| WO | 2006/009490 A1 | 1/2006 |
| WO | 2008/127653 A2 | 10/2008 |
| WO | 2018/036879 A1 | 3/2018 |

OTHER PUBLICATIONS

Gao et al., "Anterior Segment Prosthesis Development: Evaluation of Expanded Polytetrafluoroethylene as a Sclera-Attached Prosthetic Material", Cornea vol. 15, No. 2, 1996, pp. 210-214.

Goho, AM Artificial Cornea Mimics Natural Counterpart, A new material could increase the availability of corneal transplants, May 22, 2008, https://www.technologyreview.com/s/410170/artificial-cornea-mimics-natural-counterpart/.

Hicks et al., "Keratoprostheses: Advancing Toward a True Artificial Cornea", Surv Ophthalmol., vol. 42, No. 2, Sep.-Oct. 1997, pp. 175-189.

International Preliminary Report on Patentability received for PCT Patent Application No. PCT/US2019/037301, mailed on Dec. 24, 2020, 8 pages.

International Search Report and Written Opinion received for PCT Patent Application No. PCT/US2019/037296, mailed on Oct. 15, 2019, 15 pages.

International Search Report and Written Opinion received for PCT Patent Application No. PCT/US2019/037301, mailed on Oct. 7, 2019, 13 pages.

Jacob-LaBarre, "Caldwell DR: Development of a new type of artificial cornea for treatment of endstage corneal diseases," in Gebelein CG, Dunn RL (eds): Progress in Biomedical Polymers, New York, Plenum Press, 27-39, (1990).

Khan et al., "Keratoprosthesis: an update," Current Opinion in Ophthalmology, 12:282-287 (2001).

Kiang et al., "Surface epithelialization of the type I Boston keratoprosthesis front plate: immunohistochemical and high-definition optical coherence tomography characterization", Graefes Arch Clin Exp Ophthalmol, vol. 250, 2012, pp. 1195-1199.

KPMG International, Future State 2030: The global megatrends shaping governments, 2014, 80 pages.

Krishna et al., "Expanded polytetrafluoroethylene as a substrate for retinal pigment epithelial cell growth and transplantation in age-related macular degeneration", Br. J. Ophthalmol, vol. 95, 2011, pp. 569-573.

Lamberts et al., "A new alloplastic material for ophthalmic surgery," Ophthalmic Surg., 9:35-42, (1978).

Legeais et al., "A new fluorocarbon for keratoorosthesis," Cornea, 11:538-545, (1992).

Legeais et al., "A second generation of biointegrable keratoprosthesis. First in viva evaluation (abstract)," Invest Ophthalmol Vis. Sci., 37 (Suppl):1450, (1996).

Legeais et al., "Annual Meeting Abstract Issue", Arvo., vol. 32, No. 4, Mar. 15, 1991, pp. 1-2.

Legeais et al., "Expanded fluorocarbon for keratoprosthesis cellular ingrowth and transparency," Exp. Eye Res., 58:41-52, (1994).

Legeais et al., "Expanded polytetrafluoroethylene and transparency (abstract)," Invest Ophthalmol. Vis. Sci., 33 (Suppl):992, (1992).

Legeais et al., "Keratoprosthesis with biocolonizable microporous fluorocarbon haptic," Arch. Ophthalmol., 113:757-763, (1995).

Legeais et al., "Keratoprosthesis: a comparative study of three different microporous polymers and first application in human eyes (abstract)," Invest Ophthalmol. Vis. Sci., 32 (Suppl):778, (1991).

Legeais et al., "Pouliquen Y Advances in artificial corneas (abstract)," Invest Ophthalmol Vis. Sci., 36 (Suppl):1466, (1995).

Legeais et al., "Surgical management of corneal perforation with expanded polytetrafluoroethylene (Gore-Tex)," Ophthalmic Surg., 22:213-217, (1991).

Levy, "An artificial cornea is in sight, thanks to biomimetic hydrogels," D. Stanford Report, Sep. 13, 2006, https://news.stanford.edu/news/2006/september13/cornea-091306.html.

Liu et al., "Graphite/poly (vinyl alcohol) hydrogel composite as porous ringy skirt for artificial cornea", Materials Science and Engineering, C 29, 2009, pp. 261-266.

Ma et al., "Corneal epithelialisation on surface-modified hydrogel implants," J. Mater Sci. Mater Med., 22:663-670, (2011).

OECD, "OECD Science, Technology and Innovation Outlook 2016", 2016, pp. 1-18.

Stoiber et al., "Biological Response to a SupraDescemetic Synthetic Cornea in Rabbits," Arch. Ophthalmol., 122:1850-1855 (2004).

Vijayasekaran et al., "Histologic Evaluation During Healing of Hydrogel Core-and-Skirt Keratoprostheses the Rabbit Eye", Cornea, vol. 16, No. 3, 1997, pp. 352-359.

Wang et al., "Preparation an in-vitro characterization of BC/PVA hygrogel composite for its potential use as artificial cornea material," Materials Science and Engineering C 30:214-218 (2010).

White et al., "Proplast" for keratoprosthesis, Ophthalmic Surg., 19:331-333, (1988).

Xiang et al., "T-style keratoprosthesis based on surface-modified poly (2-hydroxyethyl methacrylate) hydrogel for cornea repairs", Materials Science and Engineering, C 50 ,2015, pp. 274-285.

International Preliminary Report on Patentability received for PCT Patent Application No. PCT/US2019/037296, mailed on Dec. 24, 2020, 9 pages.

Lee et al., "Chapter 6 : Corneal Suturing Techniques," Ophthalmic Microsurgical Suturing Techniques, Jan. 2007, pp. 49-59.

Roland Berger Strategy Consultants, "Trend Compendium 2030," Retrieved on Sep. 9, 2023 from URL : https://espas.secure.europarl.europa.eu/orbis/document/trend-compendium-2030, Jan. 1, 2011, pp. 1-145.

(56) References Cited

OTHER PUBLICATIONS

Goho, A. M., "Artificial Cornea Mimics Natural Counterpart: A new material could increase the availability of corneal transplants", MIT Technology Review, Retrived on Oct. 30, 2023, URL: https://www.technologyreview.com/s/410170/artificial-cornea-mimics-natural-counterpart/ , May 22, 2008, pp. 1-5.

Legeais et al., "A second generation of biointegrable keratoprosthesis. First in viva evaluation (abstract)," Investigative Ophthalmology & Visual Science, 37 (Suppl):1450, (1996).

Legeais et al., "Expanded polytetrafluoroethylene and transparency (abstract)," Investigative Ophthalmology & Visual Science, 33 (Suppl):992, (1992).

Legeais et al., "Keratoprosthesis: a comparative study of three different microporous polymers and first application in human eyes (abstract)," Investigative Ophthalmology & Visual Science, 32 (Suppl):778, (1991).

EPITHELIALIZING MICROPOROUS BIOMATERIAL FOR USE IN AVASCULAR ENVIRONMENTS AND IN CORNEAL IMPLANTS

CROSS-REFERENCE TO RELATED APPLICATION

This application is a U.S. 371 Application of International Application PCT/US2019/037301, filed Jun. 14, 2019, which claims the benefit of U.S. Provisional Application No. 62/684,843, filed Jun. 14, 2018, both of which are herein incorporated by reference in their entirety.

FIELD

The present disclosure relates generally to biomaterials, and more specifically, to a microporous biocomposite that is suitable for surgical implantation in an avascular environment and which enables a stable bio-interface and sustained epithelization directly on the surface of the microporous biocomposite in the avascular environment.

BACKGROUND

The cornea generally refracts and focuses light onto the retina and serves as a protective barrier for the intraocular components of the eye. The cornea is subject to a host of diseases, genetic disorders, and trauma that can cause opacity of what should otherwise be an optically transparent window to the retina.

Although surgical procedures exist to replace damaged or diseased corneas with live tissue corneas taken from donor eyes, donor corneas may not be available, the underlying condition of the damaged eye may be such that donor cornea failure or rejection is likely, and/or the patient's physiology may be such that a donor cornea failure or rejection is likely.

In cases where implantation of a donor cornea is not viable, implantation of an artificial cornea is a potential alternative treatment. Keratoprosthesis is the surgical implantation of an artificial cornea to replace part of or all of a damaged or diseased cornea. The primary challenges facing keratoprostheses have been biointegration complications and extrusion of the device from the eye. Other complications include infection, retroprosthetic membrane formation, inflammation, glaucoma, lack of mechanical durability and optical fouling.

A number of approaches to solving the issue of artificial cornea device rejection have been attempted. One approach involves keratoprostheses having a core and skirt type construction. The core and skirt type devices generally have a nonporous optical core for visual restoration and a skirt for bio-integration with the eye tissue surrounding the skirt.

However, such conventional core and skirt type constructions have not exhibited optimal device anchoring and long-term optical patency.

SUMMARY

According to one example ("Example 1"), a biocompatible biocomposite comprises (1) a polymer scaffold having a thickness less than about 100 µm and including nodal structures that extend from at least one surface of said polymer scaffold; and (2) a hydrophilic coating on the polymer scaffold; wherein said biocomposite is configured for the sustained viability of epithelial cells on a surface of said biocomposite in an avascular environment.

According to another example ("Example 2"), further to Example 1, the polymer scaffold is a microporous biomaterial comprising an expanded fluoropolymer membrane having a node and fibril microstructure where the nodes are interconnected by the fibrils and pores are formed by voids located between the nodes and fibrils, and the nodal structures extend from a first surface to a second surface of said polymer scaffold.

According to another example ("Example 3"), further to Example 1, the polymer scaffold is a microporous biomaterial comprising an expanded non-fluoropolymer membrane having a node and fibril microstructure where the nodes are interconnected by the fibrils and pores formed by the voids located between the nodes and fibrils, and the nodal structures extend from a first surface to a second surface of said polymer scaffold, According to another example ("Example 4"), further to Example 2 or Example 3, the pores have a size greater than about 30 µm.

According to another example ("Example 5"), further to any of Examples 2-4, the hydrophilic coating coats said nodes, said fibrils, and said nodal structures.

According to another example ("Example 6"), further to any of Examples 2, 4, or 5, the microporous biomaterial is an expanded polytetrafluoroethylene (ePTFE) membrane having said node and fibril microstructure.

According to another example ("Example 7"), further to any of Examples 2, or 4-6, the polymer scaffold is an ePTFE membrane having said nodal structures thereon, wherein said nodal structures are islands of ePTFE attached to and raising from a surface of said ePTFE membrane.

According to another example ("Example 8"), further to any of Examples 2, or 4-7, the polymer scaffold is a three-layered structure comprising a first ePTFE membrane containing thereon said nodal structures, a second ePTFE membrane containing said nodal structures, and a biocompatible adhesive positioned between said first and second ePTFE membranes, wherein said nodal structures are pillars formed of ePTFE.

According to another example ("Example 9"), further to any of Examples 1-8, the hydrophilic coating comprises poly(tetrafluoroethylene-co-vinyl alcohol) or polyvinyl alcohol.

According to one example ("Example 10"), an artificial cornea comprises: a central core including a polymeric corneal substitute; and a microporous biocomposite according to any one of Examples 1-9.

According to another example ("Example 11"), further to Example 10, the central core is formed of a material configured to permit epithelial cell growth thereon,

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

DETAILED DESCRIPTION

Persons skilled in the art will readily appreciate that various aspects of the present disclosure can be realized by any number of methods and apparatus configured to perform the intended functions. It should also be noted that the accompanying drawing figures referred to herein are not necessarily drawn to scale, but may be exaggerated to illustrate various aspects of the present disclosure, and in that regard, the figures should not be construed as limiting. It is to be appreciated that the terms "microporous biomaterial" and "biomaterial" may be used interchangeably herein. In addition, the terms "microporous biocomposite", "biocomposite", and "biocomposite material" may be interchangeably used.

The present invention is directed to a microporous biocomposite that is suitable for surgical implantation in an avascular environment. The microporous biocomposite includes (1) a porous scaffold having a thickness less than about 100 μm and which is formed of nodal structures that extend to at least one surface of the porous scaffold and (2) a hydrophilic coating on the microporous biomaterial. In exemplary embodiments, the nodal structures extend from a first surface (e.g., bottom surface) of the porous scaffold to a second surface (e.g., the top surface). In at least one embodiment, the porous scaffold is a microporous biomaterial with a nodal structure that extends from a first surface to a second surface of the microporous biomaterial. In some embodiments, the microporous biomaterial is radially expanded. In additional embodiments, the hydrophilic coating is a node and fibril coating. In some embodiments, the nodal structures are free-standing and/or vertically oriented. In addition, the microporous biocomposite allows for the integration and sustained viability of epithelial cells on the surface thereof as well as tissue integration (i.e., ingrowth) and the internal colonization of the biomaterial with other cell types, such as, for example, corneal keratocytes and fibroblasts. In at least one embodiment, the microporous biocomposite may be incorporated into an artificial corneal implant or in other avascular mesoplants.

Figure 12A:
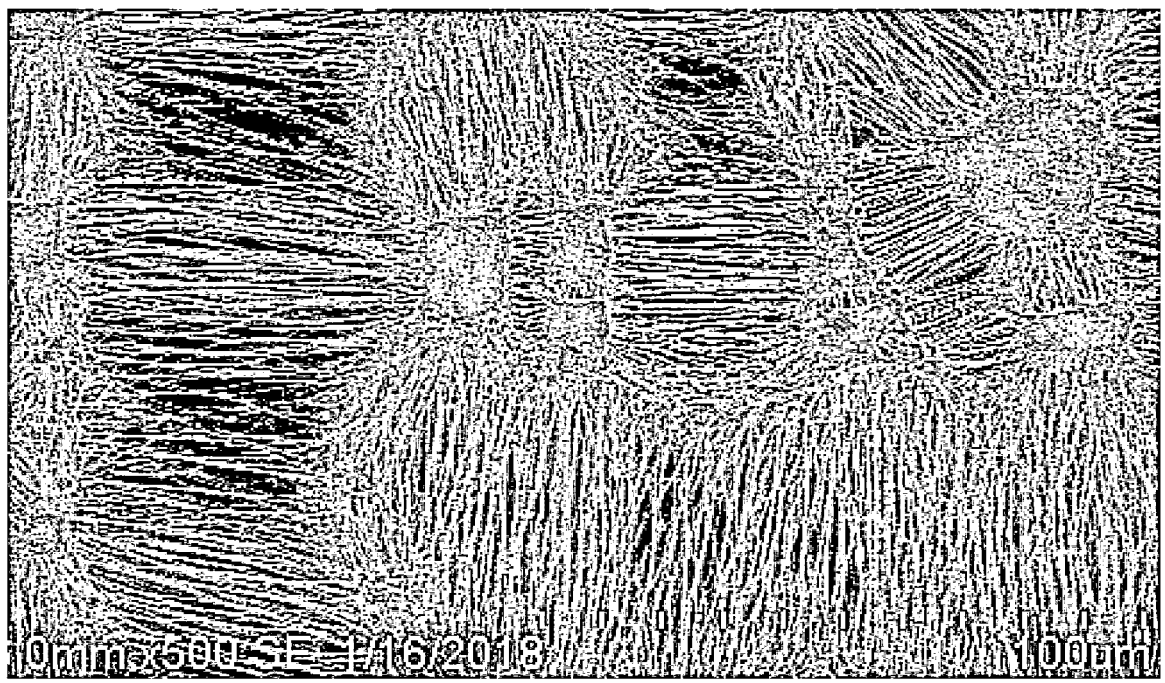
FIG. 12A is a scanning electron micrograph (SEM) of a top surface of an ePTFE membrane suitable for use in the biocompatible biocomposite in accordance with at least one embodiment.
Figure 12B:
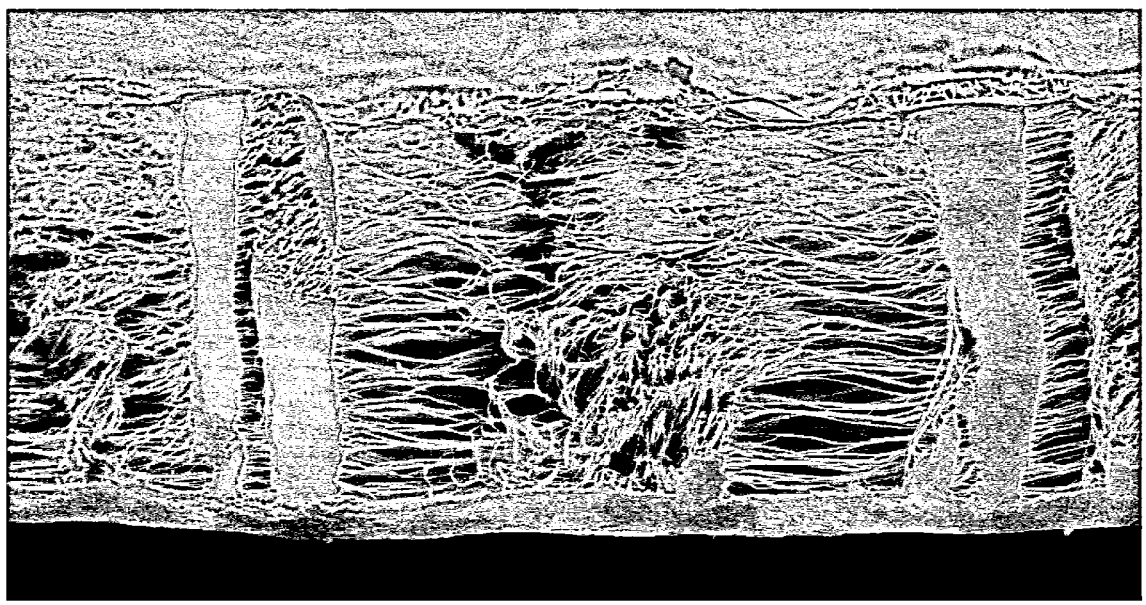
FIG. 12B is a scanning electron micrograph (SEM) of the cross-section of the ePTFE membrane of FIG. 12A.
Figure 13:
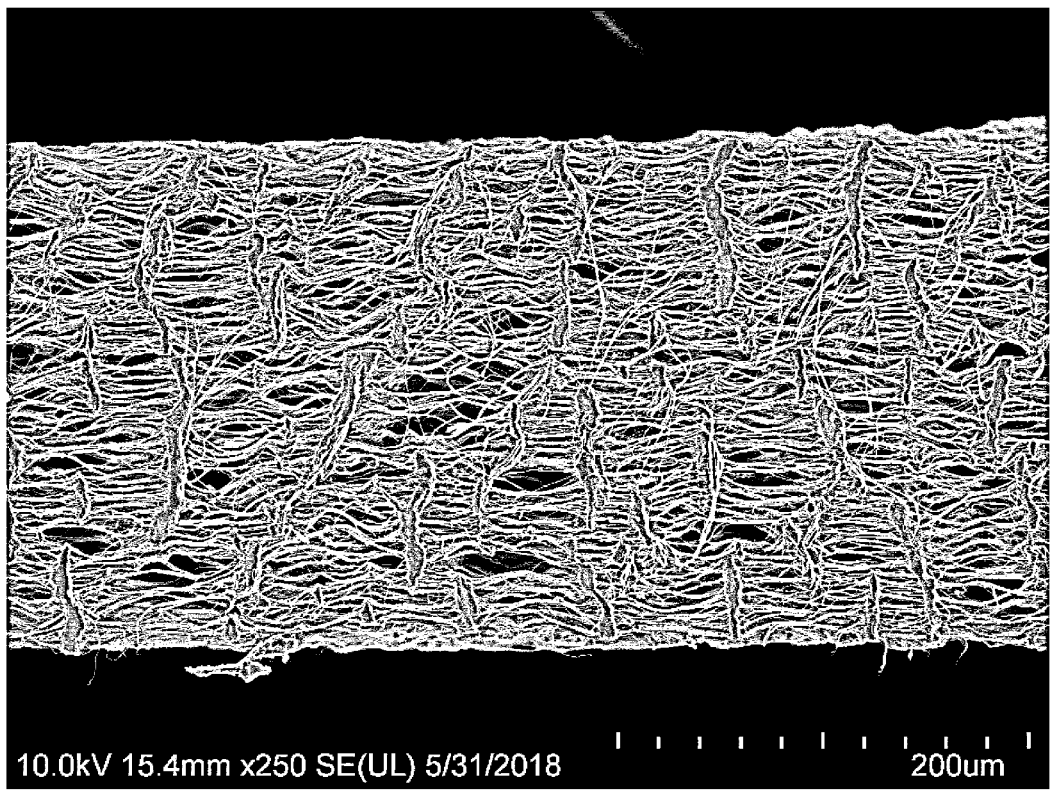
FIG. 13 is a scanning electron micrograph (SEM) of an ePTFE (vascular graft) membrane having an average nodal spacing from 35 to 100 microns and a thickness from about 110 microns to about 170 microns in accordance with at least one embodiment.
Figure 14:
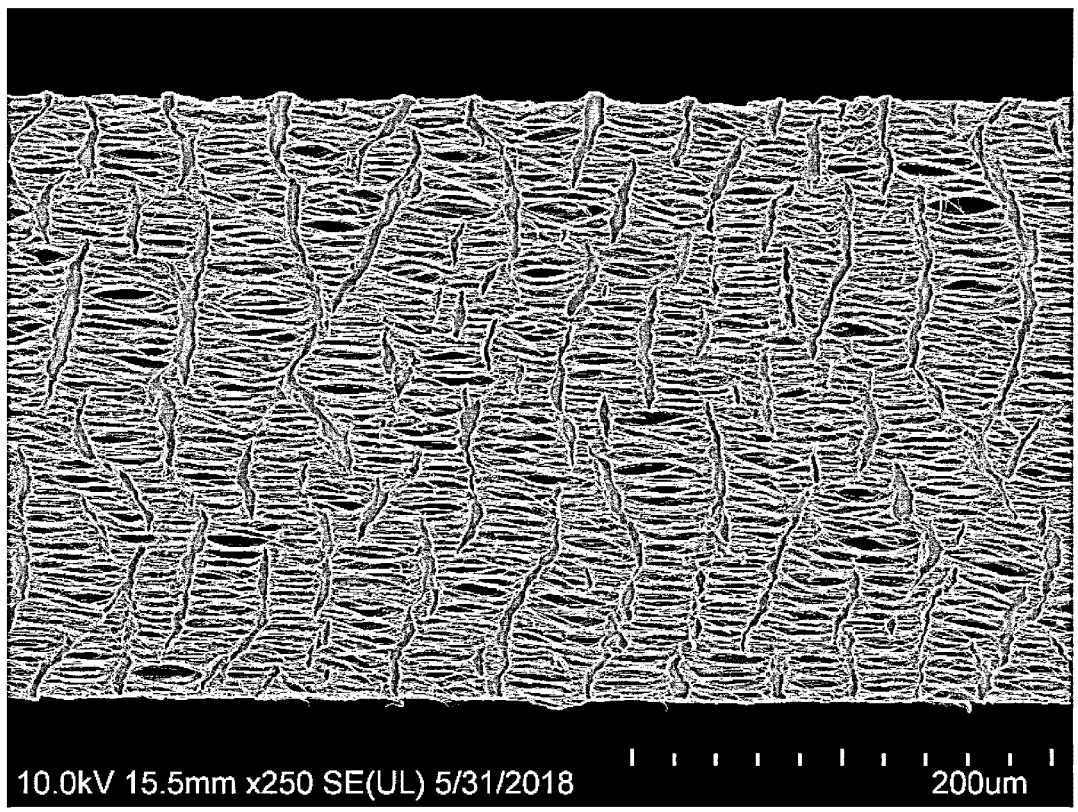
FIG. 14 is a scanning electron micrograph (SEM) of an ePTFE membrane having an average nodal spacing of 40 microns and a thickness of approximately 300 microns in accordance with at least one embodiment.

In exemplary embodiments, the porous scaffold is a microporous biomaterial. The microporous biomaterial may be a microporous expanded polymer membrane, such as a microporous expanded fluoropolymer membrane that has a node and fibril microstructure where the nodes are interconnected by the fibrils and the pores are the voids or space located between the nodes and fibrils throughout the membrane. In some embodiments, one or more perforation processes may be utilized to form a plurality of macro- or micro-sized discrete perforations in the microporous biomaterial (i.e., the polymer scaffold). An exemplary node and fibril microstructure is expanded polytetrafluoroethylene (ePTFE), such as is described in U.S. Pat. No. 3,953,566 to Gore. In at least one exemplary embodiment, the microporous polymer membrane is an expanded polytetrafluoroethylene (ePTFE) membrane. The ePTFE membranes for use in the biocomposite are characterized by nodes interconnected by thin fibrils. While not intending to be limiting, expanded polytetrafluoroethylene (ePTFE) membranes prepared generally in accordance with the methods described in U.S. Pat. No. 3,953,566 to Gore, U.S. Pat. No. 7,306,729 to Bacino et al., U.S. Patent Publication No. 2004/0173978 to Bowen et al., U.S. Pat. No. 5,476,589 to Bacino, or U.S. Pat. No. 5,183,545 to Branca et al., U.S. Pat. No. 5,476,589 to Bacino, U.S. Patent Publication No. 2016/0367947 to Hollenbaugh, et al., or U.S. Patent Publication No. 2010/0381293 to Towler may be used herein. For example, FIG. 12A is a scanning electron micrograph (SEM) of a top surface of an ePTFE membrane formed in accordance with the teachings of U.S. Patent Publication No. 2010/0381293 to Towler. FIG. 12B is a cross section of the same ePTFE membrane. FIG. 13 is an ePTFE membrane with an average nodal spacing of 35 to 100 microns (or from 60 microns to 80 microns, from 40 microns to 75 microns, or from 30 microns to 55 microns) and a thickness from about 110 microns to about 170 microns. Another ePTFE membrane for use in the microporous biocomposite is shown in FIG. 14, which is an ePTFE membrane having an average nodal spacing of 40 microns (ranging from 30 microns to 60 microns) and a thickness of approximately 300 microns. It is to be appreciated that other fluoropolymer membranes are considered to be within the purview of the invention provided that they can be processed to form a microporous membrane that is biocompatible and has a node and fibril microstructure.

The term "ePTFE" is utilized herein for convenience and is meant to include not only expanded polytetrafluoroethylene (ePTFE), but also expanded modified polytetrafluoroethylene (PTFE) and expanded copolymers of PTFE, such as are described in U.S. Pat. No. 5,708,044 to Branca, U.S. Pat. No. 6,541,589 to Baillie, U.S. Pat. No. 7,531,611 to Sabol et al., U.S. Pat. No. 8,637,144 to Ford, and U.S. Pat. No. 9,139,669 to Xu et al.

In some embodiments, the microporous biomaterial is an expanded non-fluoropolymer membrane that has a node and fibril microstructure. Non-limiting examples of suitable expanded non-fluoropolymers include porous poly (p-xylylene) (ePPX) as taught in U.S. Patent Publication No. 2016/0032069, porous ultra-high molecular weight polyethylene (eUHMWPE) as taught in U.S. Pat. No. 9,926,416 to Sbriglia, porous ethylene tetrafluoroethylene (eETFE) as taught in U.S. Pat. No. 9,932,429 to Sbriglia, porous polylactic acid (ePLLA) as taught in U.S. Pat. No. 7,932,184 to Sbriglia, et al., porous vinylidene fluoride-co-tetrafluoroethylene or trifluoroethylene [VDF-co-(TFE or TrFE)] polymers as taught in U.S. Pat. No. 9,441,088 to Sbriglia and copolymers and combinations thereof. Porous hydrogels (e.g., poly-HEMA) may be utilized herein as a non-fluoropolymer polymer. It is to be appreciated that other non-fluoropolymer polymers are considered to be within the scope of the invention so long as they can be processed to form a microporous membrane that is biocompatible and has a node and fibril microstructure.

Woven materials, non-woven materials, and electrospun fibers or nanofibers in the form of a sheet or other non-woven form may alternatively be used as a scaffold (e.g., in place of an ePTFE membrane) to form the biocomposite material.

It is to be appreciated that reference is made herein with respect to expanded polytetrafluoroethylene (ePTFE) for ease of discussion. However, it is to be understood that any suitable expanded fluoropolymer or non-fluoropolymer membrane, woven or non-woven material, or electrospun material may be used interchangeably with any "ePTFE" mentioned above.

Figure 1:
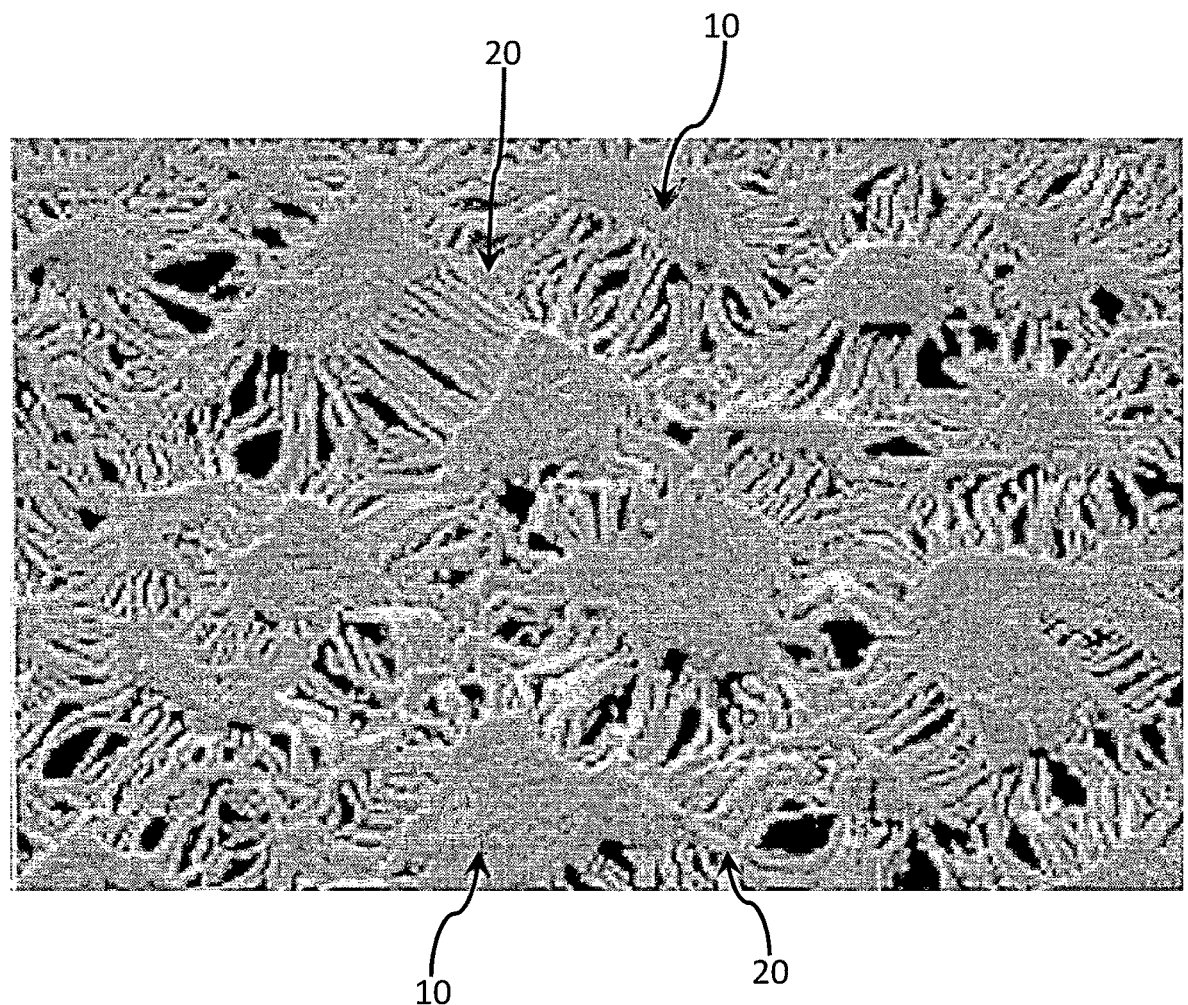
FIG. 1 is a scanning electron micrograph depicting a radially expanded ePTFE with a microstructure where the fibrils emanate from the nodes in all directions in accordance with at least one embodiment.
Figure 2:
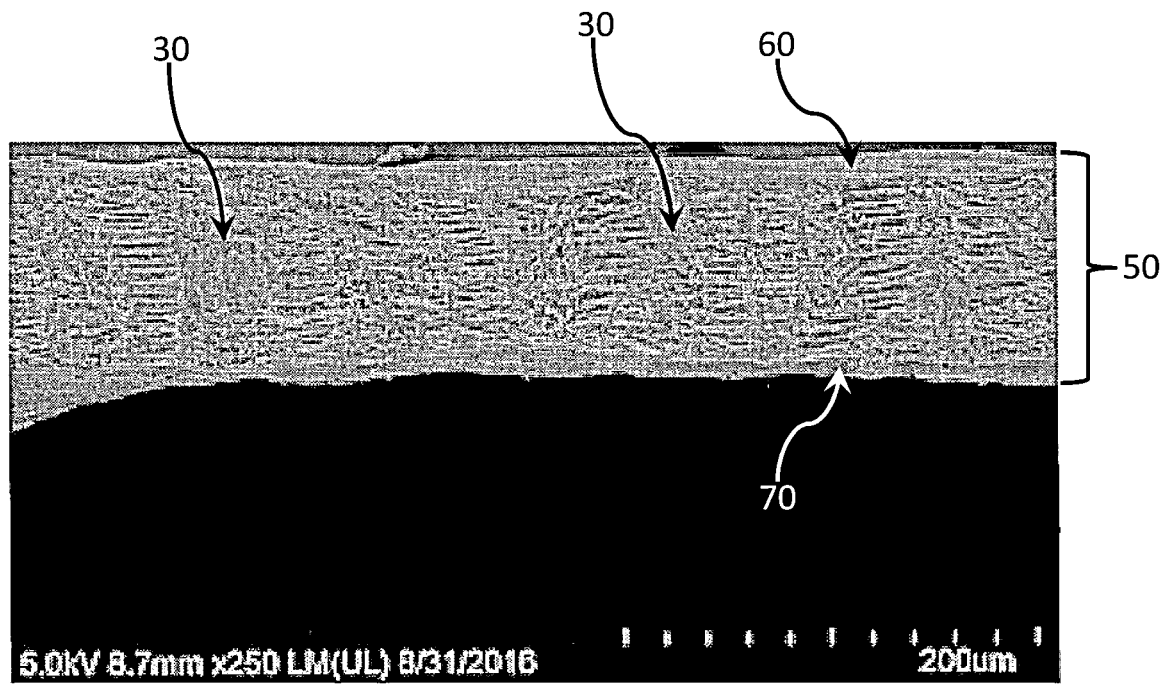
FIG. 2 is a scanning electron micrograph of a cross-section of a radially expanded ePTFE membrane that has vertically oriented nodal structures through the membrane in accordance with at least one embodiment.

In preparing the microporous biomaterial, the ePTFE may be subjected to a radial expansion, such as that described in U.S. Pat. No. 5,321,109 to Boss, et al. The radial expansion of the ePTFE creates a unique node and fibril microstructure where the fibrils 20 emanate from the nodes 10 in all directions (e.g., radially extend), such as is shown in FIG. 1. The radially-oriented fibrils 20 impart high strength to biaxial tensile loading within the plane of the membrane. In some embodiments, the ePTFE membrane has a thickness from about 50 µm to about 100 µm, from about 50 µm to about 90 µm, from about 50 µm to about 80 µm, or from about 50 µm to about 70 µm. Additionally, as shown in FIG. 2, the ePTFE membrane 50 has vertically oriented nodal structures 30 that span the thickness of the ePTFE membrane 50 (i.e., from the top surface 60 of the ePTFE membrane 50 to the bottom surface 70 of the ePTFE membrane 50). In other embodiments, the nodal structures extend to at least one surface of the ePTFE membrane, and may not necessarily be vertically oriented.

Figure 3:
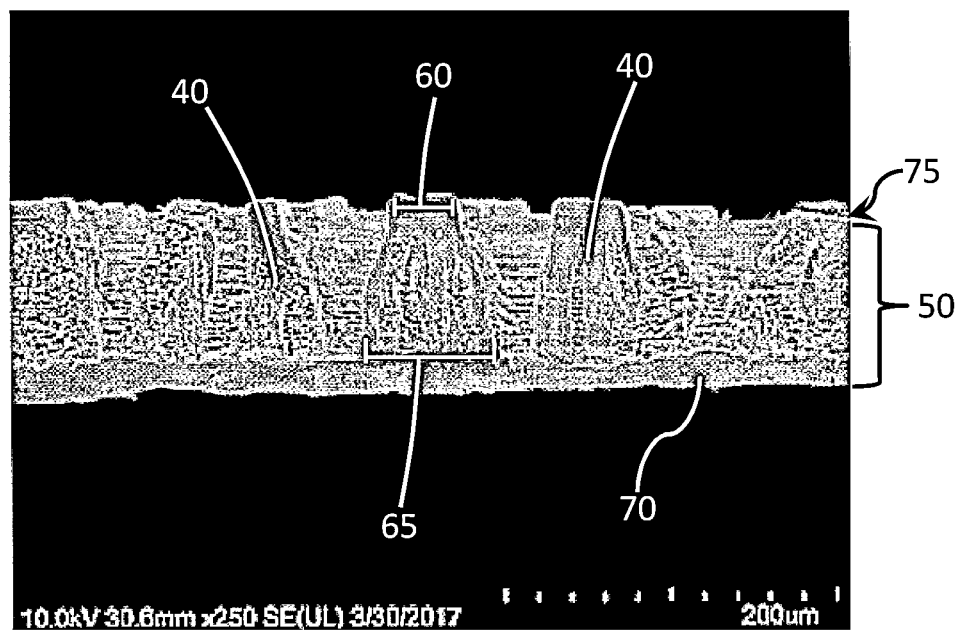
FIG. 3 is a scanning electron micrograph (SEM) of a radially expanded ePTFE depicting free standing nodal structures formed by plasma treatment in accordance with at least one embodiment.

After the radially expanded ePTFE membrane is formed, the top surface 60 of the ePTFE membrane 50 is subjected to a high surface energy treatment to alter the microstructure. One exemplary method utilized to modify the microstructure of the ePTFE membrane is to use a plasma treatment such as is taught in U.S. Pat. No. 5,462,781 to Zukowski. A second exemplary method includes U.S. Pat. No. 5,041,225 to Norma, which teaches a microporous ePTFE membrane where the internal and external surfaces of the membrane are coated with a complex formed by the combination of a hydrophilic polymer which adheres to the membrane structure and a coupling agent. The coupling agent renders the ePTFE membrane substantially hydrophilic and protein affinitive. Other process are taught in U.S. Pat. No. 5,902,745 to Butler, et al. that render an ePTFE membrane spontaneously and substantially completely water wettable by adsorbing and cross-linking the hydrophilic fluoropolymer poly(tetrafluoroethylene-co-vinyl alcohol) (HPL) into the microporous void spaces of the ePTFE membrane and onto the surfaces of the ePTFE membrane. As used herein, the term "plasma treatment" is meant to include any high energy surface treatment, such as, but not limited to, glow discharge plasma treatment, corona treatment, ion beam treatment, and the like. The plasma treatment effectively removes the fibrils from the surface of the ePTFE membrane, leaving free standing nodal structures 40 (e.g., not interconnected by fibrils), such as is shown in FIG. 3. These nodal structures 40 formed by the plasma treatment rise from the bottom surface 70 of the ePTFE membrane 50 to the top surface 60 of the ePTFE membrane. In other words, the bases 65 of the nodal structures 40 comprise the inner surface of the microporous biocomposite and the tops 60 of the nodal structures 40 comprise the top surface of the microporous biocomposite. The plasma treatment also increases the effective pore diameter of the ePTFE membrane 50, which allows better accessibility to the bottom surface 70 of the ePTFE membrane 50. The pore size of the ePTFE membrane may be greater than about 30 µm and less than about 100 µm. The inter-nodal distance at or near the top surface 60 of the nodal structures may be from about 20 µm to about 100 µm or from about 50 µm to about 70 µm. The plasma treatment creates an ePTFE membrane that has an effective pore diameter that is substantially larger on the plasma treated side (i.e., top surface 75) then on the non-plasma treated side (i.e., bottom surface 70).

Following plasma treatment, the ePTFE membrane is rendered hydrophilic through a coating process that preserves the nodal architecture of the plasma treated ePTFE membrane. In one embodiment, the ePTFE is rendered hydrophilic (e.g., water wettable) by adsorbing and cross-linking a hydrophilic, hydrogel fluoropolymer such as poly (tetrafluoroethylene-co-vinyl alcohol) (HPL) onto the nodes and fibrils of the ePTFE microstructure as well as on the surface of the ePTFE membrane (including the nodal structures). Such a process is taught generally in U.S. Pat. No. 5,902,745 to Buttler, et al. In an alternative embodiment, polyvinyl alcohol (PVA) may be used as the hydrophilic wetting agent, rather than HPL. The hydrophilic coating on the nodal structures and on the nodes and fibrils of the ePTFE membrane forms the microporous biocomposite.

In an alternate embodiment, an ePTFE membrane may be subjected to a pre-conditioning process to form "islands" of ePTFE on the surface of an ePTFE membrane. These "islands" of ePTFE are attached to and raise above the underlying ePTFE structure. The "islands" of ePTFE may be formed by subjecting the precursor ePTFE membrane to a high energy surface treatment (e.g., plasma treatment) followed by a heating step as taught in U.S. Patent Publication No. U.S. Pat. No. 7,615,282 to Lutz. et al. or U.S. Pat. No.

Figure 11A:
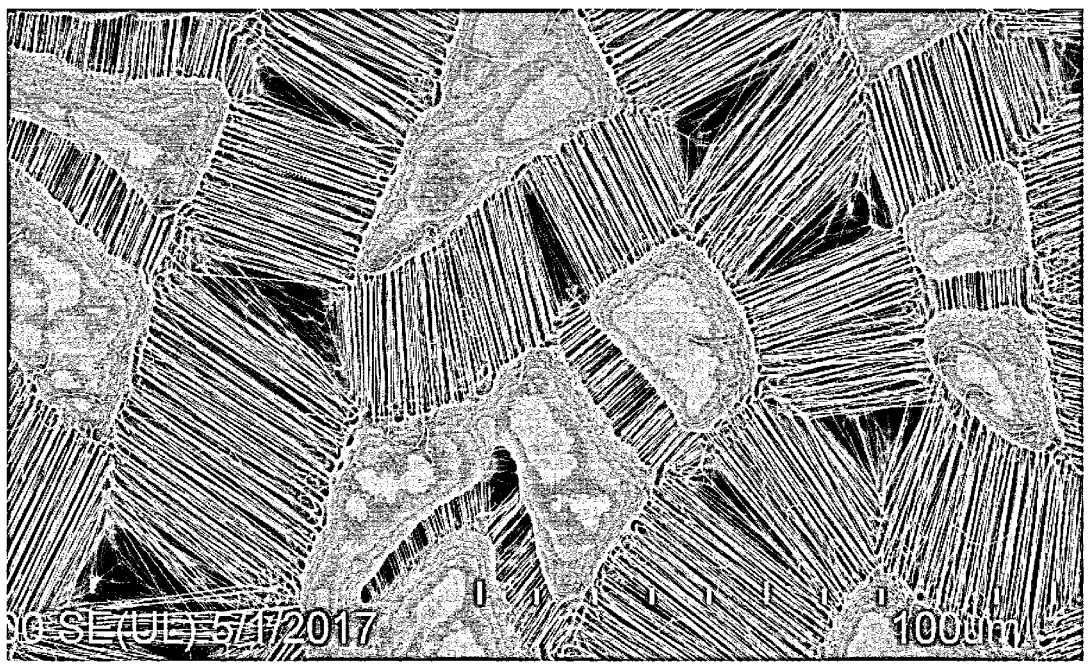
FIG. 11A is a scanning electron micrograph (SEM) of the top surface of an ePTFE membrane depicting islands of ePTFE in accordance with at least one embodiment.
Figure 11B:
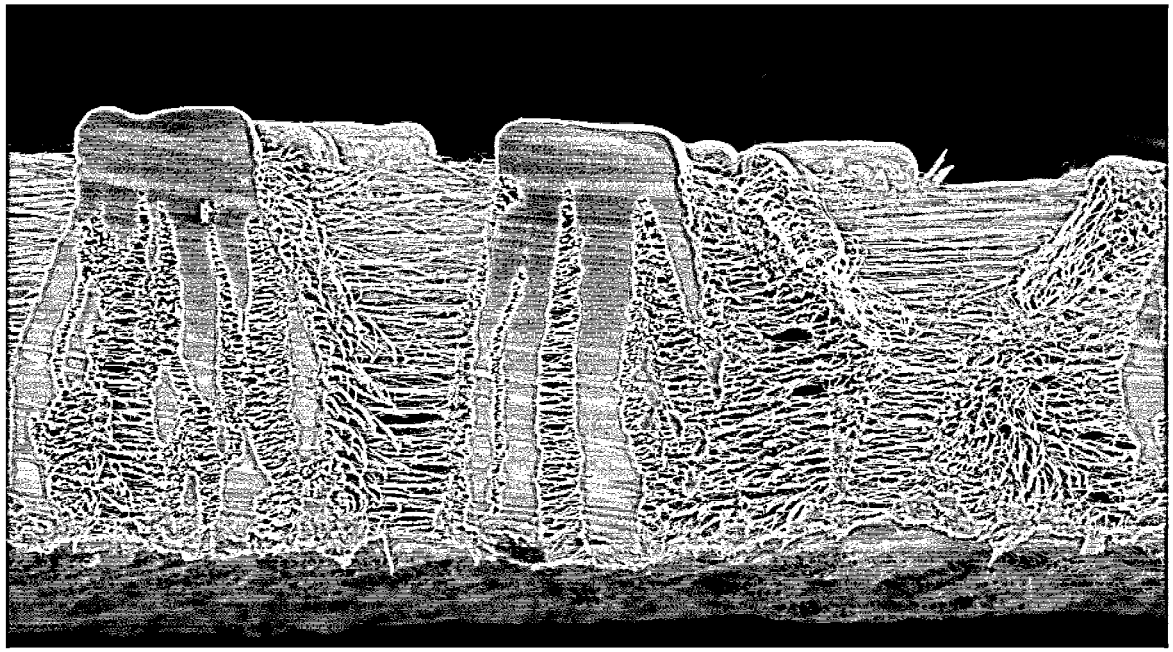
FIG. 11B is a scanning electron micrograph (SEM) of the cross-section of the ePTFE membrane of FIG. 11A in accordance with at least one embodiment.

7,740,020 to Lutz et al. A scanning electron micrograph (SEM) of the top surface of such an ePTFE membrane is depicted in FIG. 11A. A cross-section of the ePTFE membrane is shown in the SEM of FIG. 11B. The "islands" act as free-standing, vertically oriented nodal structures, which may then be subjected to a hydrophilic coating as discussed above. In other embodiments, one or more surface pre-conditioning processes may be utilized to form layers exhibiting a preferred microstructure (e.g., wrinkles, folds, or other geometric out-of-plane or undulating structures), such as is explained in U.S. Pat. No. 9,849,629 to Zaggl. Such surface pre-conditionings may facilitate a bolder early inflammatory phase after surgery, providing an early stable interface between the artificial cornea and the eye tissue with which it interfaces.

The node and fibril coating of the hydrophilic polymer permits water to not only be absorbed into the hydrophilic coating (e.g. HPL) but also allows the voids/pores in the ePTFE membrane to be filled with water. The microporous biocomposite has an adsorbed water content of less than 50% as determined by the formula $H_2O$ (wt %)=$[W_{hydrated} - W_{dry}]/W_{hydrated}$ 100% prior to implantation. However, after implantation, the adsorbed water content substantially increases due to the incorporation of water into the hydrophilic coating and into the pores of the ePTFE membrane. The hydrophilic coating on the ePTFE membrane allows the membrane to "wet out" and become visually translucent. Importantly, the microporous biocomposite allows for the integration and sustained viability of epithelial cells on the surface of thereof in an avascular environment. The microporous biocomposite also allows for tissue integration into the internal microstructure of the ePTFE and the sustained viability of these tissues in an avascular environment.

Figure 9:
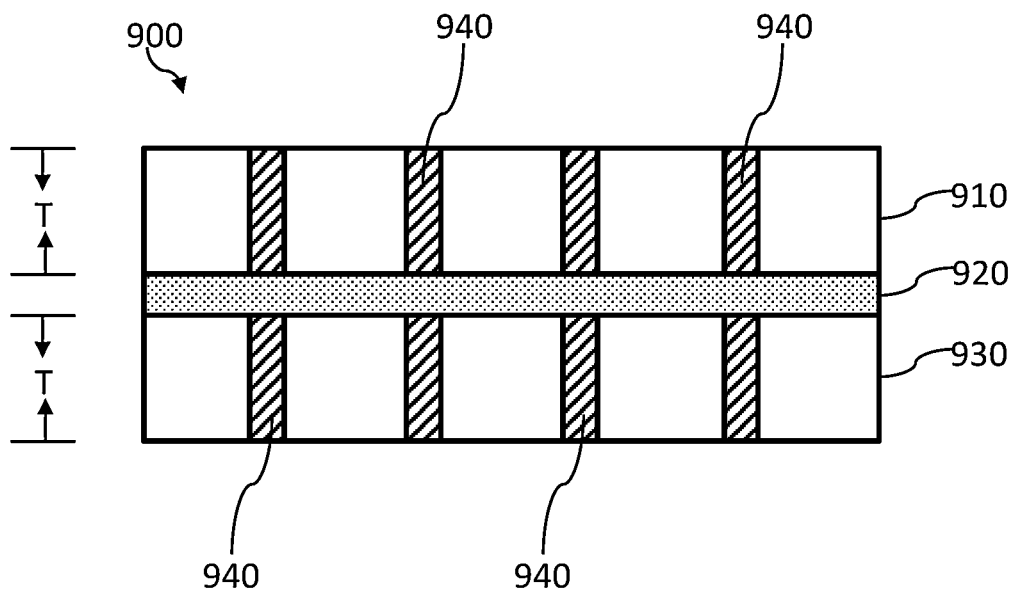
FIG. 9 is a schematic illustration of a three-layered biocomposite material in accordance with at least one embodiment.

In an alternate embodiment, the microporous biocomposite may be a three-layered structure formed of ePTFE membranes and a biocompatible adhesive as is depicted generally in FIG. 9. As shown in FIG. 9, the microporous biocomposite 900 includes a first ePTFE membrane 910, a second ePTFE membrane 920, and a biocompatible adhesive 930 such as fluorinated ethylene propylene (FEP) to adhere the first and second ePTFE membranes 910, 920 to each other. Pillars 940 interconnect the top and bottom portions of the ePTFE membranes and provide structural support for the microporous biocomposite. As with the embodiment discussed above, each ePTFE membrane has a thickness (T) that is about 100 μm.

Figure 10:
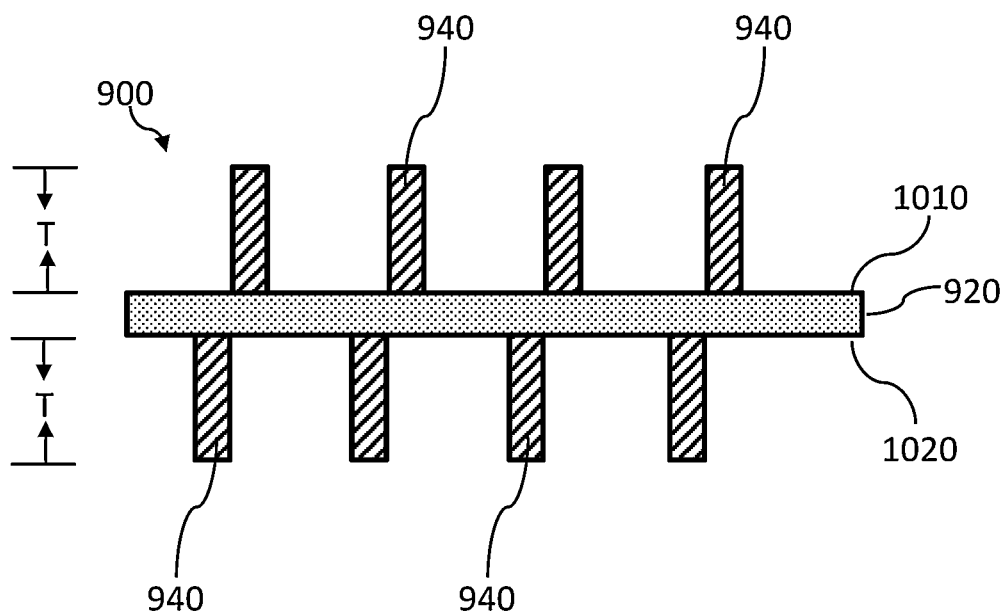
FIG. 10 is a schematic illustration of a three-layered biocomposite made by forming structural pillars on the surface of the ePTFE membrane in accordance with at least one embodiment.

In some embodiments, depicted in FIG. 10, the pillars 940 of microporous biocomposite 900 may be printed or otherwise laid down on support substrates 1010,1020, such as, for example, ePTFE membranes. The pillars 940 may themselves be made out of ePTFE. The support substrates 1010, 1020 are adhered to each other with a biocompatible adhesive, such as fluorinated ethylene propylene (FEP). In such an embodiment, the pillars 940 have a thickness less than about 100 μm. A hydrophilic coating may then be applied to coat the pillars 940 and the ePTFE substrates to form a microporous biocomposite.

Figure 4:
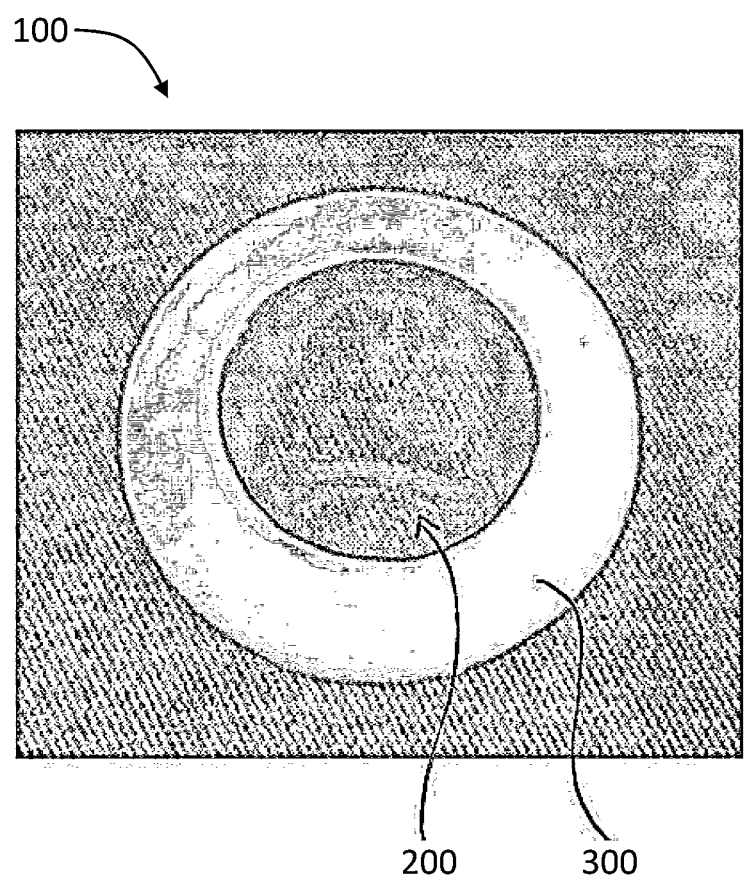
FIG. 4 is an image of an exemplary artificial cornea having clear cornea substitute region and a white region surrounding the clear cornea substitute region that includes the microporous biocomposite in accordance with at least one embodiment.
Figure 15A:
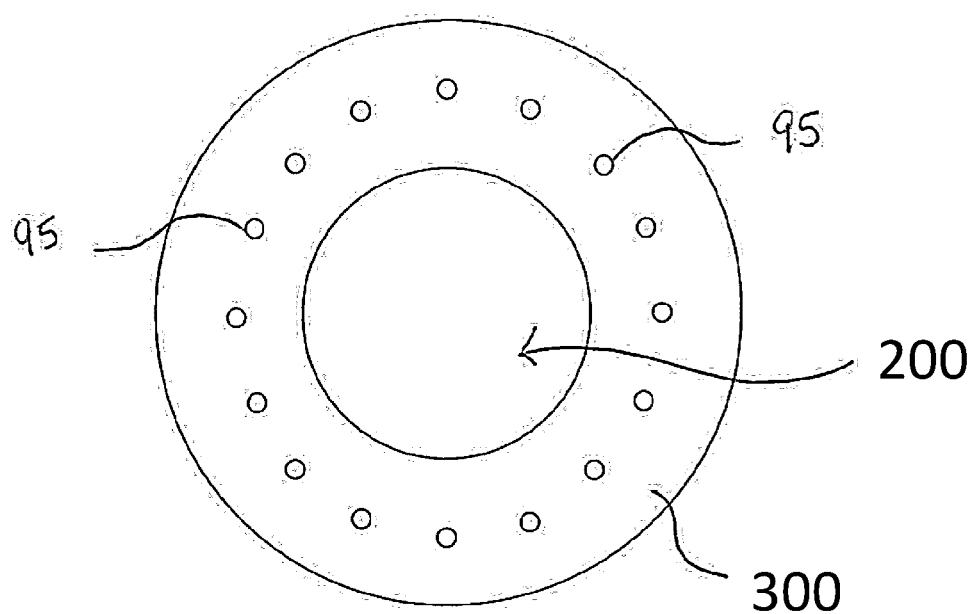
FIG. 15A is a schematic illustration of the top view an artificial cornea with macro-perforations in the tissue integration skirt in accordance with at least one embodiment.
Figure 15B:
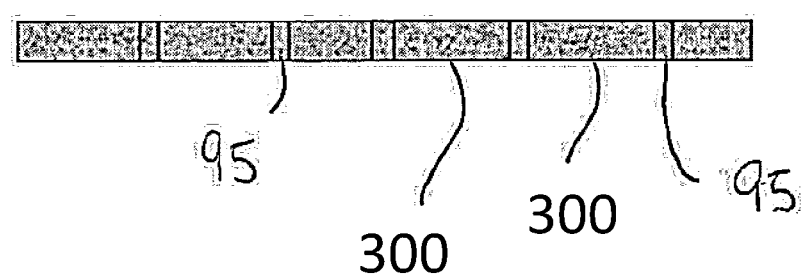
FIG. 15B is a schematic illustration of the cross-sectional view of the artificial cornea of FIG. 15A in accordance with at least one embodiment.

In at least one embodiment, the microporous biocomposite is incorporated into an artificial corneal implant. As used herein, the terms "artificial corneal implant" or "artificial cornea" are meant to include all forms of artificial corneas, including synthetic corneas, keratoprostheses, and the like. Turning to FIG. 4, an image of an exemplary artificial cornea 100 is depicted. The artificial cornea 100 is an implantable medical device that operates as a synthetic replacement for diseased corneas, damaged corneas, or corneas otherwise requiring replacement. The artificial cornea 100 includes an optical element 200 and the microporous biocomposite 300 at least partially surrounding the optical element 200. The optical element 200 may be formed of a synthetic polymeric material. Because of the hydrophilic coating on the ePTFE membrane, the ePTFE is able to wet out and become clear in the presence of water. Thus, when such an artificial cornea 100 is implanted in an eye, microporous biocomposite 300 becomes clear like the optical element 200 and is not visible to the naked eye. Advantageously, the microporous biocomposite does not appreciable change its dimension (volume) after being fully absorbed by water. Additionally, the microporous biocomposite 300 permits tissue ingrowth and the attachment of epithelial cells directly on the microporous biocomposite in an avascular environment whereas the optical element is configured to resist tissue ingrowth and attachment. In some embodiments, the optical element 200 may be modified to facilitate cell adhesion and/or proliferation, such as, for example, the formation of an organized monolayer of epithelial cells on the optical element 200. Additionally, the optic element may be non-porous such that no cellular integration or infiltration may occur. As depicted in FIGS. 15A and 15B, macroscopic, discrete perforations 95 may be formed in the microporous biocomposite 300 by any suitable perforation process known to one of skill in the art.

Figure 5:
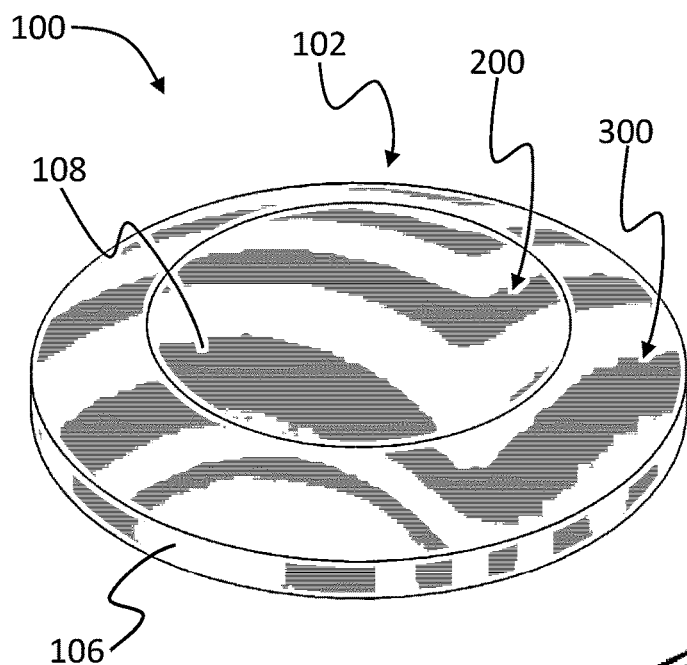
FIG. 5 is a schematic illustration of an artificial cornea in accordance with at least one embodiment.

FIG. 5 depicts an artificial cornea 100 according to some embodiments. As shown, the artificial cornea 100 includes an optical element 200 and a tissue integration skirt 300 that is formed of the microporous biocomposite. Similar to the embodiment depicted in FIG. 4, macroscopic, discrete perforations 95 may be formed in the tissue integration skirt 300 (see, e.g., the tissue integration skirt 300 of FIGS. 15A-15B). The microporous biocomposite is positioned on the eye such that the tops 60 of the nodal structures 40 are facing outwardly (e.g., away from the inner portion of the eye) so that the nodal structures enable tissue ingrowth and the growth of epithelial cells directly on the surface of the biocomposite material. The spaces between the nodal structures permit tissue ingrowth into the biocomposite material. In addition, the biocomposite material allows the integration and sustained viability of other cell types such as, but not limited to, keratocytes and fibroblasts, and/or other corneal cells.

The artificial cornea 100 has an anterior side 102 and a posterior side 104 opposite the anterior side 102. When implanted, the anterior side 102 generally faces or is otherwise exposed to an outside environment, while the posterior side 104 faces an interior of the eye. Thus, when implanted, the artificial cornea 100 is a barrier between the interior of the eye and the outside environment. The artificial cornea 100 may include a front profile corresponding with a generally circular, elliptical or ovular shape. One or more of the anterior or posterior optical surfaces 102, 104 may be curved or non-curved, such that an edge profile of the artificial cornea may correspond with the anterior and posterior optical surfaces being curved or non-curved. As used herein, the term "optical surface" is meant to denote a surface which significantly contributes to the formation of an image in the scope of visual acuity by being the primary refractive surface in the optical path. In addition, the optical surface participates in the formation of a clear, distortion-free image.

Figure 6:
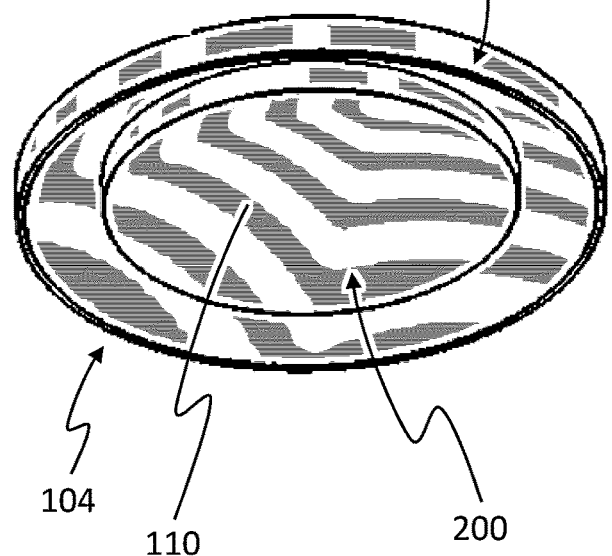
FIG. 6 is a rear perspective view of the artificial cornea construction of FIG. 5 in accordance with at least one embodiment.

In some embodiments, an outer peripheral surface 106 that extends about the periphery of the artificial cornea 100 and may be regularly or irregularly shaped (e.g., scalloped, spoked, star-shaped, etc.). The artificial cornea 100 includes an anterior optical surface 108 and a posterior optical surface 110. As discussed in greater detail below, the anterior and posterior optical surfaces 108, 110 of the artificial cornea 100 generally correspond to anterior and posterior optical surfaces 260, 265 of the optical element 200, and are thus shaped accordingly. For example, as shown in FIGS. 5 and 6, the anterior side 102 is generally convex and a posterior side 104 is generally concave.

Figure 7:
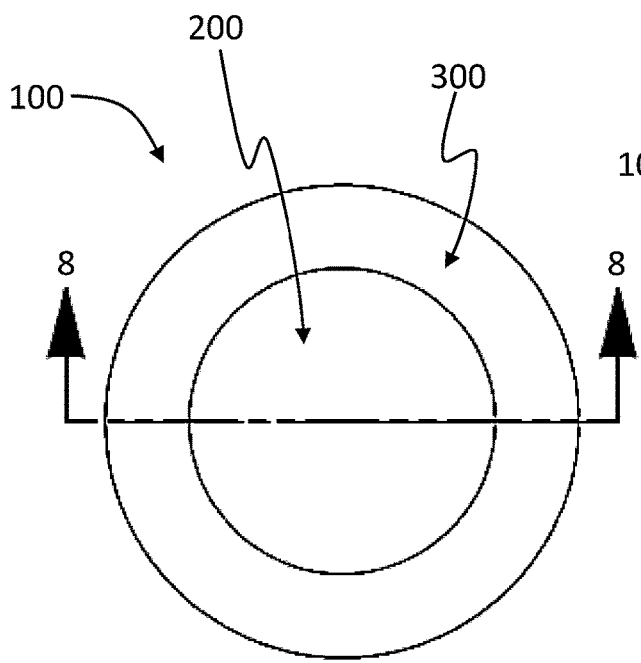
FIG. 7 is a top view of the artificial cornea construction of FIG. 5 in accordance with at least one embodiment.
Figure 8:
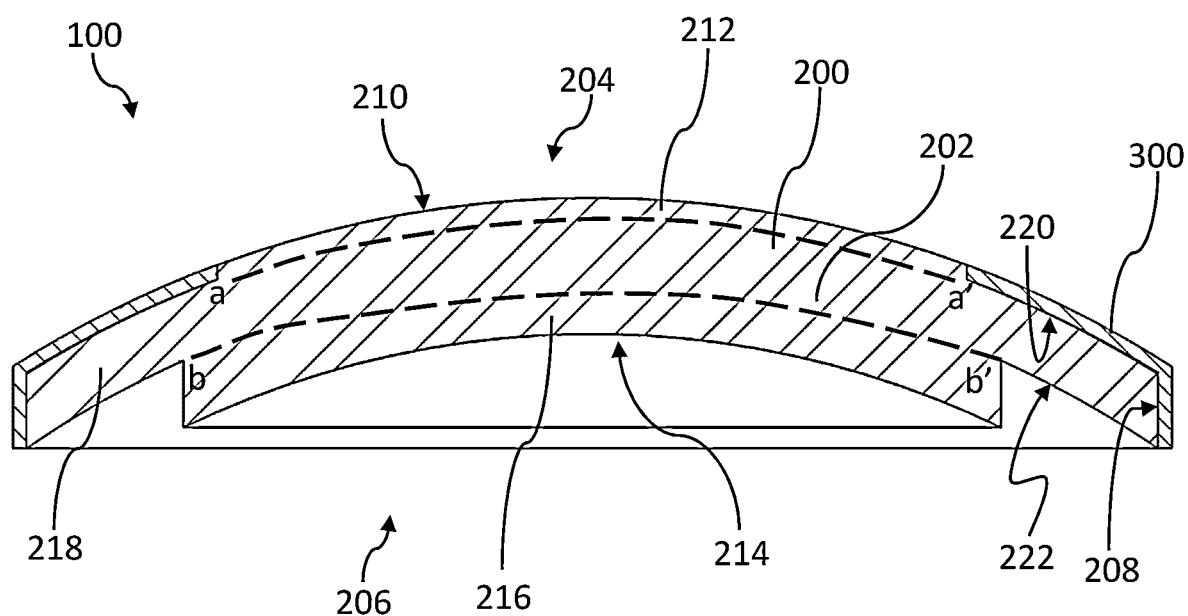
FIG. 8 is a cross sectional view of the artificial cornea construction of FIG. 5 taken along line 7-7 in accordance with at least one embodiment.

FIG. 8 shows a cross-sectional view of the artificial cornea 100 taken along line 8-8 of FIG. 7. As shown in FIG. 8, the artificial cornea 100 includes an anterior side 204 and a posterior side 206. The anterior side 204 generally faces or is otherwise exposed to an outside environment, while the posterior side 206 faces the eye (e.g., eye tissue and eye interior). In various examples, the anterior side 204 is generally convexly curved, while the posterior side 206 is generally concavely curved. As shown, the artificial cornea 100 may include a body (e.g., a disk) 202 that has an anterior protrusion 212 (extending above dashed line a-a'), and a posterior protrusion 216 (extending below dashed line b-b'). As used herein, the term "protrusion" is meant to define a region which protrudes, projects, or otherwise extends above or beyond the normal body (e.g., a disk) contour or surface. The anterior and posterior protrusions 212, 216 may be generally circularly shaped. In some embodiment, the anterior and posterior protrusions 212 and 216 are dissimilarly sized and/or shaped.

In various embodiments, the posterior side 206 of the optical element 200 includes a posterior optical surface, such as posterior optical surface 214 located on at least a portion of the anterior protrusion 216. In some embodiments, the posterior optical surface 214 operates as an interface between the optical element 200 of the artificial cornea 100 and an interior of the eye, and defines at least a portion of the posterior side 206 of the optical element 200. The posterior optical surface 214 corresponds to the posterior optical surface 110 of the artificial cornea 100 (see FIG. 6). In various embodiments, the posterior optical surface 214 is a smooth surface capable of high light transmission and is generally free of surface defects or imperfection such as scratches, pits, or gouges. In some embodiments, the posterior optical surface 214 is generally curved or nonlinear. For example, as shown in FIG. 8, the posterior optical surface 214 is concave.

In some embodiments, the optical element 200 includes a posterior protrusion or a protrusion of the body 202 that extends posteriorly from the body 202. For example, as shown in FIG. 8, the optical element 200 includes a posterior protrusion 216. The posterior protrusion 216 may be a protrusion of all of or less than all of the posterior side 206 of the body 202. In some embodiments, the posterior optical surface 214 corresponds to a posterior surface of the posterior protrusion 216. In other embodiments, the posterior optical surface 214 extends across an entire posterior side 206 of the body 202 and defines the posterior side 206 of the body 202.

In some embodiments, the anterior protrusion 212, a portion of the body 202, and a portion of the posterior protrusion 216 form a core portion of the body 202 of the optical element 200. In some examples, the core portion of the body 202 is formed of a different material than is a remainder of the body 202 of the optical element 200. In some such examples, the core of the body 202 may be formed of an optically transparent and tissue ingrowth inhibiting material as described herein.

In the embodiment depicted in FIG. 8, the posterior optical surface 214 is positioned on at least a portion of the posterior protrusion 216. The posterior optical surface 214 may have a concave geometry to its surface. The anterior and posterior optical surfaces 210, 214 are disc-shaped members that operate as an optically transparent window to the retina when implanted in a patient's eye. As used herein, the term "optical element" is intended to refer to a surface which significantly contributes to the formation of an image in the scope of visual acuity by being the primary refractive surface in the optical path. The optical surface 210 is the interface between the artificial cornea 100 and the external environment and is located on at least a portion of the anterior protrusion 212. The optical element 200 is also capable of high light transmission and is ideally largely free of surface defects. In numerous embodiments, the optical element 200 is optically transparent in that the optical element 200 operates as a synthetic alternative to an otherwise normally functioning cornea.

As shown in FIG. 8, the body 202 may be generally disk shaped with an annular flange 218 about its outer perimeter. In some embodiments, the body 202 is formed of a synthetic biocompatible material. An annular attachment layer 300 is oriented around the anterior protrusion 235. As used herein, the term "disk" is intended to refer to a substantially circular or elliptical shape which may be flat or have some curvature (e.g., whether concave or tapered). Additionally, the term "annular" as used herein is intended to include any circular, elliptical, scalloped, star shaped, spoke-like, or any suitable geometry for the outer perimeter of the device.

FIG. 8 shows a cross-sectional view of the artificial cornea 100 taken along line 8-8 of FIG. 7. The artificial cornea 100 includes the microporous biocomposite 300, which is coupled to the optical element 200 without compromising the optical performance of the optical element 200. As shown in FIG. 8, the microporous biocomposite 300 is coupled to the optical element 200 along the peripheral surface 208 and the anterior surface 220, without extending across the anterior and posterior optical surfaces 210 and 214 of optical element 200, and without extending across the posterior surface 222 of optical element 200. In some embodiments, the peripheral surface 208 thus forms or defines a first tissue attachment and/or ingrowth region. Similarly, in some embodiments, the anterior surface 220 forms or defines a second tissue attachment and/or ingrowth region. The microporous biocomposite 300 enables the attachment of epithelial cells directly on the biocomposite. In addition, the microporous biocomposite 300 is oriented around at least the perimeter of the optical element 200 on peripheral surface 208 and allows bio-integration of tissue and cells at the perimeter of optical element 200. The positioning of the microporous biocomposite 300 around the perimeter of the optical surface 200 allows for the artificial cornea 100 to be naturally integrated into the patient's eye over time through tissue ingrowth and epithelial growth on the surface of the biomaterial. Additionally, the bio-integration of the microporous biocomposite 300 reduces the ingress of bacteria, which reduces the chance of infection.

In some embodiments, microporous biocomposite is sized and applied to the optical element 200. In some examples, the microporous biocomposite is cut to size, such as through one or more laser cutting or other suitable cutting processes known to those of skill in the art. The microporous biocomposite 300 is coupled to the optical element 200 without extending across the anterior and posterior optical surfaces 210 and 214 of optical element 200. Additional material coating processes may be utilized to apply one or more drug or antimicrobial coatings, such as metallic salts (e.g. silver carbonate) and/or organic compounds (e.g. chlorhexidine diacetate), to the biocomposite so long as the coating process does not destroy the nodal structures.

The optical element 200 may be formed from a number of suitable materials including, but not limited to, fluoropolymers selected from a copolymer of tetrafluoroethylene (TFE) and perfluoroalkyl vinyl ether (PAVE), a copolymer of tetrafluoroethylene (TFE) and perfluoromethyl vinyl ether (PMVE), a copolymer of tetrafluoroethylene (TFE) and perfluoroethyl vinyl ether (PEVE), a copolymer of tetrafluoroethylene (TFE), a copolymer of tetrafluoroethylene (TFE) and perfluoropropyl vinyl ether (PPVE), a copolymer of TFE and hexafluoropropylene (FEP), perfluoropolymers containing TFE as a comonomer, perfluoroalkoxy alkanes (PFA), perfluoropolyethers, or can comprise silicone, poly (methyl methacrylate) (PMMA), hydrogel, polyurethane, and combinations thereof.

In some embodiments, the optical element 200 may be formed from a material that includes a copolymer of TFE and PMVE, which is uniquely formed to have excellent mechanical properties while being substantially non-cross-linkable, i.e., free of cross-linking monomers and curing agents. The copolymer contains between 40 and 80 weight percent PMVE units and complementally between 60 and 20 weight percent TFE units. The lack of cross-linking systems ensures that the material is highly pure and, unlike some thermoset TFE/PMVE elastomers, is ideally suited as an implantable biomaterial. Advantages include excellent biocompatibility, high tensile strength, high clarity, high abrasion resistance, high purity, adequate elasticity, and ease of processing due to the thermoplastic and the non-cross-linkable structure of the copolymer. The copolymer is thermoplastic and amorphous. It also is of high strength and can be used as a bonding agent particularly suited for bonding porous PTFE to itself or to other porous substances at room or elevated temperatures. It may also be used to bond nonporous materials including polymers such as nonporous PTFE. U.S. Pat. No. 7,049,380 to Chang, et al. further illustrates and describes such copolymers of TFE and PMVE.

The materials forming the body 202 of optical element 200 generally include microstructures that minimize, inhibit, or even prevent tissue ingrowth and attachment. Configuring the body 202 of the optical element 200 in such a manner helps minimize a potential for the surrounding corneal tissue or other eye tissue to grow into or across the optical element 200, as the ingrowth and/or attachment of corneal tissue or other associated eye tissue to the body 202 of the optical element has a tendency to degrade or otherwise foul the optical performance of the optical element 200. In some embodiments, in addition to a microstructure of the optical element 200 being configured to minimize or avoid tissue ingrowth, one or more surface texturing or coating processes may be utilized to minimize the potential for tissue to grow into or across the optical element 200.

In some examples, the optical element 200 may have a refractive index from 1.2 to 1.6, or from 1.3 to 1.5. In some examples, the optical element 200 may have a light transmission in the visible light transmission range (wavelength of from 400-700 nm) of greater than 50%, or greater than 80%. Additives such as cross-linking agents, biologically active substances (e.g., growth factors, cytokines, heparin, antibiotics or other drugs), hormones, ultraviolet absorbers, pigments, other therapeutic agents, etc., may be incorporated into the material forming the optical element 200 depending on the desired performance of the device.

Turning back to FIG. 5, it is to be appreciated that the microporous biocomposite 300 is coupled to the optical element 200 without compromising the optical performance of the optical element 200. That is, the microporous biocomposite 300 is sized and shaped such that, when coupled to the optical element 200, the anterior and posterior optical surfaces 210 and 214 of the optical element 200 remain unobstructed. The microporous biocomposite 300 may thus be an annularly shaped member that, when coupled with the optical element 200, extends peripherally about one or more of the anterior and posterior optical surfaces 210 and 214. In some embodiments, the microporous biocomposite 300 may be applied to the optical element 200 according to any known attachment methods including, but not limited to adhesives, thermal bonding, pressure, or molding.

In some examples, the artificial cornea 100 may be subjected to one or more processes to achieve a desired shape. In some examples, these processes may achieve a desired shape that conforms to the shape of the penetration made in the patient's cornea. In some examples, these processes may achieve a desired shape and/or contour of one or more of the optical surfaces of the artificial cornea 100 (e.g., for proper light refraction). Such processes include the use of glass lenses made to a specific radius of curvature that is directly transferred to the optical element via a secondary molding procedure consistent with the description above. In other examples, a refractive surface is additionally or alternatively achieved through the use of machined surfaces using stainless steel or other suitable materials. In some examples, such surfaces could also be made to have special curvatures that offsets inherent optical distortions specific to the patient's eye.

In some embodiments, the microporous biocomposite 300 is applied to the optical element 200 such that the posterior side 206 of the optical element 200 remains uncovered or otherwise exposed. That is, in various embodiments, the posterior side 206 of the optical element 200 remains free from coverage by the microporous biocomposite 300. For example, as shown in FIG. 8, the tissue integration element 300 is applied to the optical element 200 such that the posterior side 206, including the posterior optical surface 214 of the artificial cornea 100 is exposed or not otherwise covered by an anchoring material. Thus, in various examples, the microporous biocomposite 300 is applied to the optical element 200 such that the microporous biocomposite 300 does not otherwise contact the posterior side 206 of the optical element 200 including the posterior optical surface 214.

In some embodiments, the microporous biocomposite 300 is applied to the optical element 200 such that a portion of the anterior surface 210 of the optical element 200 is covered or otherwise concealed by the microporous biocomposite 300. In some examples, the microporous biocomposite 300 is applied to the anterior side 204 of the optical element 200 such that the anterior side of the artificial cornea 100 is smooth. In such examples, a transition between the anterior optical surface 210 of the artificial cornea 100 and the portion of the microporous biocomposite 300 applied to the anterior side 204 of the optical element 200 is smooth (e.g., free of protrusions, gaps, etc.). A smooth transition between the anterior optical surface 210 and the tissue integration element 300 provides that the anterior side 204 of the implanted artificial cornea 100 does not cause discomfort or irritation, or interfere with other portions of the patient's anatomy (e.g., such as the patient's eyelid). In addition, the incorporation of the microporous biocomposite 300 along a portion of the anterior side 204 of artificial cornea 100 promotes a proliferation of tissue ingrowth and epithelial formation along a portion of the anterior side 204 of the artificial cornea 100. It is to be appreciated that, while the microporous biocomposite 300 is shown in FIG. 8 as being applied across an entirety of the peripheral surface 208 of the annular protrusion 218, in some examples, the microporous biocomposite 300 may applied to a portion of less than all of the peripheral surface 208.

In some embodiments, the microporous biocomposite 300 may be comprised of a plurality of discrete sections that are independently and separately coupled to the optical element 200. For example, a first section or portion of the microporous biocomposite 300 may be applied to the anterior optical surface 220 while a second distinct section or portion of the microporous biocomposite 300 is applied to the peripheral surface 208 of optical element 200. In some examples, these discrete sections or portions may be applied such that they abut or otherwise contact one another in a manner that facilitates a continuous coverage of the intended portions of the optical element 200. Thus, in some examples, a plurality of discrete sections of polymer material may be applied to the optical element 200 from a microporous biocomposite 300 that is generally smooth and continuous.

In some embodiments, the artificial cornea illustrated and described herein is implanted in conjunction with a penetrating keratoplasty surgical procedure wherein a full-thickness section of tissue is removed from the diseased or injured cornea using a surgical cutting instrument, such as a trephine or a laser. In various examples, a circular full-thickness plug of the diseased or damaged cornea is removed, leaving a tissue bed of corneal tissue to which the artificial cornea 100 can be affixed. In such a configuration, a portion of or all of the posterior side 104 of the artificial cornea 100 is suspended above the interior of the eye. That is, a portion of or all of the posterior side 104 of the artificial cornea 100 is not supported by the existing corneal tissue of the eye. In cases involving a full thickness excision of the cornea, the cornea is generally removed from epithelium to endothelium. In some instances, a diseased portion of the anterior cornea can be excised and the corneal device can be positioned on the residual bed of cornea to repair a defect or diseased portion.

In some embodiments, the surgical implantation method may require the artificial cornea 100 to be folded, deformed, or otherwise constrained prior to being implanted. In such examples, the artificial cornea is folded, deformed, or otherwise constrained and introduced into the tissue bed. In some examples, a separate constraint may operate to maintain a deformation of the artificial cornea 100 as it is being inserted or otherwise implanted into the tissue bed. In various examples, the artificial cornea 100 is sufficiently resilient such that the deformed artificial cornea can assume its undeformed geometry to occupy the tissue bed upon being released.

In other embodiments, the surgical implantation method requires undersizing the trephinated hole made in the host cornea relative to the diameter of the artificial cornea. In some examples, this is to account for the amount by which the excised host cornea grows when it experiences trauma (e.g., an incision). In some examples, such undersizing also operates to account for retraction due to partial corneal melting, post-surgery. In addition, such undersizing allows the wound to be air and liquid tight after suturing, which helps avoid infection risks due to ingress of pathogens.

In various examples, after the artificial cornea is properly positioned and oriented within the tissue bed of the existing corneal tissue, the artificial cornea is mechanically coupled to the existing corneal tissue. In various examples, one or more sutures are utilized to mechanically fasten the artificial cornea to the existing corneal tissue. In some other examples, an ophthalmic glue may additionally or alternatively be utilized for mechanically coupling the artificial cornea to the existing corneal tissue. In the case of suturing, the particular surgical suturing technique (e.g., interrupted, uninterrupted, combined, single, double, etc.) may vary based on a number of surgical indications as will be appreciated by those of skill in the art. In various examples involving the fastening of the artificial cornea to the existing corneal tissue by way of one or more sutures, the sutures generally extend into the annular flange 218 of the optical element 200 of the artificial cornea 100. In some examples, one or more sutures extend through only a portion of the annular flange 218. For example, one or more sutures may enter the anterior side 102 of the artificial cornea 100 and exit the artificial cornea 100 through the peripheral surface 208 and any tissue integration skirt material covering the peripheral surface 208 before entering the existing corneal tissue. In some examples, one or more sutures additionally or alternatively extend entirely through the annular flange 218. For example, one or more sutures enter the anterior side 102 of the artificial cornea 100 and exit the posterior surface 222 of the annular flange 218 before entering the existing corneal tissue. In one such example, the suture exiting the posterior surface 222 of the annular flange 218 may enter existing corneal tissue upon which the posterior surface 222 of the annular flange 218 is resting.

Those of skill should appreciate that mechanically fastening or affixing (e.g., suturing) of the artificial cornea 100 to the existing corneal tissue may be temporary or permanent. For instance, in some examples, sutures provide mechanical fastening of the device after an implantation procedure to implant artificial cornea 100, but subsequent tissue ingrowth into the microporous biocomposite 300 operates as a permanent mechanism for attachment.

In various embodiments, fastening the artificial cornea 100 to the existing corneal tissue operates to maintain a relative position between the artificial cornea 100 and the existing corneal tissue while corneal tissue grows into the microporous biocomposite 300, as those of skill will appreciate. Likewise, as those of skill will appreciate, fastening the artificial cornea 100 to the existing corneal tissue operates to maintain contact between the existing corneal tissue and the artificial cornea 100 while corneal tissue grows into the tissue integration element 300. Such a configuration also operates to seal the interior of the eye from the outside environment and potential ingress of bacteria.

In various examples, the sutures may comprise any suitable biocompatible material including nylon, polypropylene, silk, polyester and fluoropolymers such as ePTFE and other copolymers discussed herein.

While above-discussed embodiments include configurations where the skirt covers only a portion of the anterior surface, in some examples, the skirt may cover the entire anterior side including the anterior optical surface. Such a configuration helps facilitate the proliferation and integration of epithelial tissue across the entire anterior surface of the artificial cornea that is exposed to the external environment, which would help further biointegration. Additionally, such a configuration would increase optic wettability, and help minimize fouling. However, in certain cases, epithelial tissue growth across the entire anterior surface of the artificial cornea may be undesirable.

For example, in certain instances, diseased tissue lacks the appropriate morphology to be a clear refracting surface. In such instances, the regenerated epithelium tissue is therefore unclear and could lead to optical fouling and should be avoided.

Example

An artificial cornea of utilizing the microporous biomaterial was constructed in the following manner.

A random fluorinated copolymer consisting of approximately 50% (by wt) tetrafluoroethylene (TFE) and 50% (by wt) perfluoromethyl vinyl ether (PMVE) was made by emulsion polymerization, resulting in an average emulsion particle size of less than 100 nanometers (particle size estimated using light scattering methods). The copolymer exhibited the following properties: mean tensile strength of 31 MPa (+/−8 MPa) and mean 100% secant modulus of 3.7 MPa (+/−0.5 MPa).

Approximately 12 g of the TFE-PMVE copolymer were placed in a 40 mm diameter puck-shaped mold within a vacuum fixture. The TFE-PMVE copolymer was then compressed under vacuum into a 40 mm puck of approximately 4 mm thickness, at a temperature of about 180° C. and under about 3.45 MPa pressure for about 20 minutes.

Subsequently, four 4 mm TFE-PMVE diameter disks (e.g., one disk per corneal implant) were punched from the pucks using a die cutter and used as the starting material for the molding process described below. The weight of each disk of starting material was generally between 100-110 mg.

A disk of TFE-PMVE was placed in a compression mold having substantially the geometry to form a shape of the optical element 200. The mold was placed in a Carver press (Carver, Inc., Wabash, IN) having platens with a 523 cm$^2$ cross-sectional area and were maintained at a temperature of 180° C. The platens were then brought in contact with the mold so as to apply minimal pressure on the mold (i.e., only contact of the plate with the mold to enable heating of the mold). The mold was held under these conditions for 9 minutes. At the end of 9 minutes, the platen pressure was increased to 7 metric tons and maintained for 1 minute. After 1 minute, the mold was removed from the press and placed between heavy metal surfaces to cool. Once the mold had reached 25° C., the resulting molded fluoropolymer optic disk was carefully removed from the mold. Any excess polymer "flash," or material overflow, was cut off during the molding/removal process.

In order to facilitate nutritional transport through the polymeric corneal substitute material, holes were laser cut into the protrusion of the material, using a $CO_2$ laser (Model ML-9370F, Keyence, Inc., NJ). Two circles of 24 holes, approximately 250 μm in diameter, and 16 holes, approximately 250 μm in diameter on an 8 and 7 mm diameter circle, respectively.

Expanded polytetrafluoroethylene (ePTFE) having a density of 0.4 (+/−0.02) g/cc, matrix tensile strength of about 14,000 psi (96 MPa) in two orthogonal directions, water entry pressure of 10.2 (+/−0.6) psi (70+/−4 KPa) and thickness of about 0.1 mm was employed as the annular layers, each having an inner opening matching the anterior and posterior protrusions, respectively, of the disk.

The ePTFE employed in the annular layers was surface treated using an argon plasma. Only the side of the membrane to be exposed (i.e., the side which would face away from the disk of TFE/PMVE polymer) was surface treated with a hand-held plasma treater as described in accordance with the teaching of the U.S. Patent Publication No. 2006/0047311 to Lutz, et al. The treated samples were heat treated unrestrained at 250° C. for 15 minutes in a convection oven. The surface treatment resulted in a morphology with features having an average feature height measurement of about 8-15 μm and a peak-to-valley distance of about 40-50 μm.

To form the annular layers of the device, the ePTFE was then restrained in hoops, and holes corresponding to the anterior or posterior protrusion diameter were laser cut using the $CO_2$ laser. The laser spot size and intensity were 60 μm and 20%, respectively, and the traversing speed of the laser was 200 mm/s. Specifically, for the annular layer to be oriented on the posterior surface of the polymeric corneal substitute material, the surface treated side was oriented downward, then a hole corresponding to the posterior protrusion was cut using a $CO_2$ laser (Model ML-9370F, Keyence, Inc., NJ). Correspondingly, for the annular layer to be oriented on the anterior side of the polymeric corneal substitute material, the surface treated side was oriented upward, then a hole corresponding to the anterior protrusion was cut using a $CO_2$ laser (Model ML-9370F, Keyence, Inc., NJ). The disk of polymeric corneal substitute material was then placed so that the posterior protrusion extended through the hole in the annular layer (treated surface facing downward). Subsequently, the cut membrane with treated surface facing upward was then oriented around the anterior protrusion of the polymeric corneal substitute material.

The assembled layers of polymeric corneal material and ePTFE layers were then heated and compressed together in the following manner.

The posterior protrusion of the polymeric corneal substitute material (assembled with ePTFE layers) was centrally oriented so as to rest on a high precision planar convex BK7 lens (Edmund Optics lens with 9 mm diameter with +12 mm focal length). This allowed for shaping of the posterior protrusion to have a concave geometry. To form the precise optical surface of the anterior protrusion, a high precision planar concave N-SF11 lens (Edmund Optics lens with 9 mm diameter, −9 mm focal length, ground to 0.1115 in thickness) was placed centrally and a weight to apply about 100 KPa pressure was used on the anterior lens. The ePTFE surfaces were then compressed by precision machined parts to apply 90 KPa using gravity. Here, the annular portion and the optics (glass lens) of the assembly were compressed independently. The entire assembly was then placed in a convection oven at 180° C. for 45 minutes. The hot assembly was then removed from the oven and was permitted to cool to room temperature. The applied weight and silica lenses were then removed, and the $CO_2$ laser (Model ML-9370F, Keyence, Inc., NJ) was used to cut the outer diameter of the device to about 9.5 mm.

The keratoprosthesis was then treated using the following process:

1) The keratoprosthesis was immersed slowly edgewise into 100% isopropyl alcohol and left in the solution for 5 minutes. This forced the residual air from the porous expanded PTFE, allowing the alcohol to fully penetrate the porous annular and sealing region layers.
2) The keratoprosthesis was then soaked in a 2% (wt/vol) polyvinyl alcohol (PVA)/deionized (DI) water solution for 15 minutes.
3) The keratoprosthesis was then rinsed in DI water for 15 minutes.
4) The keratoprosthesis was then placed in a 4% glutaraldehyde/2.6% hydrochloric acid (37.6% NF grade)/DI water solution (vol/vol/vol) for 15 minutes.
5) The keratoprosthesis was then rinsed in DI water for 15 minutes.
6) The treated keratoprosthesis was then air dried.

After hydrophilic treatment, the prototypes were steam sterilized at 110° C. for 10 minutes prior to implantation.

The invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

What is claimed is:

1. A biocompatible biocomposite comprising:
a polymer scaffold having a thickness less than about 100 μm and including nodal structures that extend from at least one surface of said polymer scaffold, wherein the nodal structures are pillars that provide support to the biocompatible biocomposite; and
a hydrophilic coating on the polymer scaffold, the hydrophilic coating and the polymer scaffold defining a microstructure including pores, and
wherein the microstructure sustains viability of epithelial cells on a surface of the biocompatible biocomposite in an avascular environment.

2. The biocomposite of claim 1, wherein the polymer scaffold is a microporous biomaterial comprising an expanded fluoropolymer membrane, the microstructure having a node and fibril structure wherein the nodes are interconnected by the fibrils and the pores are formed by voids located between the nodes and fibrils, and
wherein the nodal structures extend from a first surface to a second surface of the polymer scaffold.

3. The biocomposite of claim 1, wherein the polymer scaffold is a microporous biomaterial comprising an expanded non-fluoropolymer membrane, the microstructure having a node and fibril structure where the nodes are interconnected by the fibrils and the pores formed by voids located between the nodes and fibrils, and
wherein the nodal structures extend from a first surface to a second surface of the polymer scaffold.

4. The biocomposite of claim 1, wherein the pores have a size greater than about 30 μm.

5. The biocomposite of claim 2, wherein the hydrophilic coating coats the nodes, the fibrils, and the nodal structures.

6. The biocomposite of claim 5, wherein the microporous biomaterial is an expanded polytetrafluoroethylene (ePTFE) membrane having the node and fibril microstructure.

7. The biocomposite of claim 2, wherein said polymer scaffold is an ePTFE membrane having the nodal structures thereon,
wherein the nodal structures are islands of ePTFE attached to and raising from a surface of the ePTFE membrane.

8. The biocomposite of claim 7, wherein the polymer scaffold is a three-layered structure comprising a first ePTFE membrane having a portion of the nodal structures thereon, a second ePTFE membrane having another portion of the nodal structures thereon, and a biocompatible adhesive positioned between the first and second ePTFE membranes, wherein the nodal structures are formed of ePTFE.

9. The biocomposite of claim 1, wherein the hydrophilic coating comprises poly(tetrafluoroethylene-co-vinyl alcohol) or polyvinyl alcohol.

10. An artificial cornea comprising:
a central core including a polymeric corneal substitute; and
a microporous biocomposite surrounding the central core, wherein the microporous biocomposite comprises:
a polymer scaffold having a thickness less than about 100 μm and including nodal structures that extend from at least one surface of the polymer scaffold, wherein the nodal structures are pillars that provide support to the biocompatible biocomposite; and
a hydrophilic coating on the polymer scaffold, the hydrophilic coating and the polymer scaffold defining a microstructure including pores, and
wherein the microporous sustains viability of epithelial cells of a surface of the microporous biocomposite in an avascular environment.

11. The artificial cornea of claim 10, wherein the polymer scaffold is a microporous biomaterial comprising an expanded fluoropolymer membrane, the microstructure having a node and fibril structure wherein the nodes are interconnected by the fibrils and the pores are formed by voids located between the nodes and fibrils, and
wherein the nodal structures extend from a first surface to a second surface of the polymer scaffold.

12. The artificial cornea of claim 10, wherein the polymer scaffold is a microporous biomaterial comprising an expanded non-fluoropolymer membrane, the microstructure having a node and fibril structure where the nodes are interconnected by the fibrils and the pores are formed by voids located between the nodes and fibrils, and
wherein the nodal structures extend from a first surface to a second surface of the polymer scaffold.

13. The artificial cornea of claim 10, wherein the microporous biomaterial is an expanded fluoropolymer having a node and fibril microstructure.

14. The artificial cornea of claim 10, wherein said pores have a size greater than about 30 μm.

15. The artificial cornea of claim 11, wherein the hydrophilic coating coats the nodes, the fibrils, and the nodal structures.

16. The artificial cornea of claim 15, wherein the microporous biomaterial is an expanded polytetrafluoroethylene (ePTFE) membrane having the node and fibril microstructure.

17. The artificial cornea of claim 10, wherein the polymer scaffold is an ePTFE membrane having the nodal structures thereon,
wherein the nodal structures are islands of ePTFE attached to and raising from a surface of the ePTFE membrane.

18. The artificial cornea of claim 10, wherein the polymer scaffold is a three-layered structure comprising a first ePTFE membrane having a portion of the nodal structures thereon, a second ePTFE membrane having another portion of the nodal structures thereon, and a biocompatible adhesive positioned between the first and second ePTFE membranes, wherein the nodal structures are formed of ePTFE.

19. The artificial cornea of claim 10, wherein the hydrophilic coating comprises poly(tetrafluoroethylene-co-vinyl alcohol) or polyvinyl alcohol.

20. The artificial cornea of claim 10, wherein the central core is formed of a material permitting epithelial cell growth thereon.

* * * * *